(12) United States Patent
Taki

(10) Patent No.: US 12,133,752 B2
(45) Date of Patent: Nov. 5, 2024

(54) ESTIMATION DEVICE, ESTIMATION METHOD, AND ESTIMATION PROGRAM

(71) Applicant: FUJIFILM CORPORATION, Tokyo (JP)

(72) Inventor: Tomoko Taki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 295 days.

(21) Appl. No.: 17/591,616

(22) Filed: Feb. 3, 2022

(65) Prior Publication Data
US 2022/0287665 A1    Sep. 15, 2022

(30) Foreign Application Priority Data

Mar. 12, 2021 (JP) ................. 2021-040686

(51) Int. Cl.
| | |
|---|---|
| *A61B 6/00* | (2024.01) |
| *A61B 6/03* | (2006.01) |
| *A61B 6/50* | (2024.01) |
| *G06N 3/08* | (2023.01) |
| *G06T 7/00* | (2017.01) |

(52) U.S. Cl.
CPC .............. *A61B 6/482* (2013.01); *A61B 6/032* (2013.01); *A61B 6/483* (2013.01); *A61B 6/505* (2013.01); *G06N 3/08* (2013.01); *G06T 7/0012* (2013.01); *G06T 2207/10116* (2013.01);
(Continued)

(58) Field of Classification Search
CPC ......... A61B 6/032; A61B 6/482; A61B 6/505; A61B 6/5217; A61B 6/483; A61B 6/5223; A61B 6/5235; G06T 2207/10081; G06T 2207/10116; G06T 2207/20081; G06T 2207/20084
See application file for complete search history.

(56) References Cited

U.S. PATENT DOCUMENTS

| | | | |
|---|---|---|---|
| 6,064,716 A | 5/2000 | Siffert et al. | |
| 2022/0051398 A1* | 2/2022 | Watanabe | ............ G06T 7/0012 |

FOREIGN PATENT DOCUMENTS

| | | |
|---|---|---|
| EP | 3851048 A1 | 7/2021 |
| WO | 2019208037 A1 | 10/2019 |
| WO | 2020/054738 A1 | 3/2020 |

OTHER PUBLICATIONS

Partial English language translation of the following: Notification dated Nov. 7, 2023 from the JPO in a Japanese patent application No. 2021-040686 corresponding to the instant patent application.
(Continued)

*Primary Examiner* — Dani Fox
(74) *Attorney, Agent, or Firm* — SOLARIS Intellectual Property Group, PLLC

(57) ABSTRACT

An estimation device includes at least one processor, in which the processor functions as a learned neural network that derives a result of estimation relating to a bone density of a bone part from a simple radiation image acquired by simply imaging a subject including the bone part or a DXA scanning image acquired by imaging the subject by a DXA method. The learned neural network is learned by using, as teacher data, a composite two-dimensional image representing the subject, which is derived by combining a three-dimensional CT image of the subject, and information relating to the bone density of the subject.

11 Claims, 14 Drawing Sheets

(52) U.S. Cl.
CPC ............... *G06T 2207/20081* (2013.01); *G06T 2207/20084* (2013.01); *G06T 2207/30008* (2013.01)

(56) References Cited

OTHER PUBLICATIONS

Mirella López Picazo et al. "3-D Subject-Specific Shape and Density Estimation of the Lumbar Spine From a Single Anteroposterior DXA Image Including Assessment of Cortical and Trabecular Bone", IEEE Transactions on Medical Imaging, vol. 37, No. 12, Dec. 2018, pp. 2651-2662.

Extended European Search Report dated Jun. 17, 2022, issued in corresponding EP Patent Application No. 22161114.8.

* cited by examiner

ESTIMATION DEVICE, ESTIMATION METHOD, AND ESTIMATION PROGRAM

CROSS REFERENCE TO RELATED APPLICATIONS

The present application claims priority under 35 U.S.C. § 119 to Japanese Patent Application No. 2021-040686 filed on Mar. 12, 2021. The above application is hereby expressly incorporated by reference, in its entirety, into the present application.

BACKGROUND

Technical Field

The present disclosure relates to an estimation device, an estimation method, and an estimation program.

Related Art

A dual x-ray absorptiometry (DXA) method is known as one of typical bone mineral quantification methods used for diagnosing a bone density in a bone disease, such as osteoporosis. The DXA method is a method for calculating bone mineral density from a pixel value of a radiation image obtained by performing imaging by the radiation of two types of energies by using radiation incident on and transmitted through a human body, which is attenuated by an attenuation coefficient $\mu$ ($cm^2/g$), density $\rho$ ($g/cm^3$) and a thickness t (cm), which depend on a substance (for example, a bone) that configures the human body.

In addition, various methods for evaluating the bone density using a radiation image acquired by imaging a subject have been proposed. For example, U.S. Pat. No. 6,064,716A and WO2020/054738A propose a method for estimating information relating to the bone density from an image in which the bone appears by using a learned neural network constructed by learning a neural network. In the method disclosed in U.S. Pat. No. 6,064,716A, the neural network is learned by using the image in which the bone appears acquired by simple imaging and the bone density as teacher data. In addition, in the method disclosed in U.S. Pat. No. 6,064,716A, the neural network is learned by using the image in which the bone appears acquired by the simple imaging, the bone density, and the information relating to the bone density (for example, age, gender, weight, drinking habit, smoking habit, fracture history, body fat percentage, and subcutaneous fat percentage) as the teacher data.

Note that the simple imaging is an imaging method for acquiring one two-dimensional image, which is a transmission image of the subject, by emitting the radiation to the subject once. In the following description, the radiation image acquired by simple imaging will be referred to as a simple radiation image.

However, it is desired to estimate a bone density with higher accuracy.

SUMMARY OF THE INVENTION

The present disclosure has been made in view of the above circumstances, and is to enable estimation of the bone density with high accuracy.

An aspect of the present disclosure relates to an estimation device comprising at least one processor, in which the processor functions as a learned neural network that derives a result of estimation relating to a bone density of a bone part from a simple radiation image acquired by simply imaging a subject including the bone part or a DXA scanning image acquired by imaging the subject by a DXA method, and the learned neural network is learned by using, as teacher data, a composite two-dimensional image representing the subject, which is derived by combining a three-dimensional CT image of the subject, and information relating to the bone density of the subject.

Note that in the estimation device according to the present disclosure, the composite two-dimensional image may be derived by deriving an attenuation coefficient of radiation for a composition at each position on a three-dimensional space, and projecting the CT image in a predetermined direction based on the attenuation coefficient.

In addition, in the estimation device according to the present disclosure, the information relating to the bone density may be obtained by specifying a bone region in the CT image, deriving an attenuation coefficient of radiation in the bone region, and deriving the information relating to the bone density based on the bone density at each position in the bone region, which is derived based on the attenuation coefficient of the radiation and a mass attenuation coefficient in the bone region.

In addition, in the estimation device according to the present disclosure, the information relating to the bone density may be derived by projecting the bone density at each position in the bone region in a predetermined direction.

In addition, in the estimation device according to the present disclosure, the information relating to the bone density may include at least one of a bone density per unit area, a bone density per unit volume, an evaluation value of a fracture risk of the subject, or information representing a recovery state after the bone part is treated.

In addition, in the estimation device according to the present disclosure, the processor may function as the learned neural network that derives the result of estimation relating to the bone density of the bone part from the DXA scanning image, and the learned neural network may be learned by using, as the teacher data, a low-resolution composite two-dimensional image obtained by performing processing for reducing a resolution on the composite two-dimensional image, and the information relating to the bone density of the subject.

In addition, in the estimation device according to the present disclosure, the low-resolution composite two-dimensional image may be an image in which an average value of pixel values of a plurality of adjacent pixels of the composite two-dimensional image is used as the pixel values of the plurality of adjacent pixels, and sizes of the plurality of adjacent pixels may correspond to one pixel size of the DXA scanning image.

In addition, in the estimation device according to the present disclosure, the low-resolution composite two-dimensional image may be an image obtained by performing movement average processing on the composite two-dimensional image in one direction, and the one direction is a scanning direction of the DXA scanning image.

In addition, in the estimation device according to the present disclosure, the low-resolution composite two-dimensional image may be an image generated by generating a first low-resolution image in which an average value of pixel values of a plurality of adjacent pixels of the composite two-dimensional image is used as the pixel values of the plurality of adjacent pixels, and performing movement average processing on the first low-resolution image in one direction, sizes of the plurality of adjacent pixels may correspond to one pixel size of the DXA scanning image, and the one direction may correspond to a scanning direction of the DXA scanning image.

Another aspect of the present disclosure relates to an estimation method comprising using a learned neural network that derives a result of estimation relating to a bone density of a bone part from a simple radiation image acquired by simply imaging a subject including the bone part or a DXA scanning image acquired by imaging the subject by a DXA method to derive the result of estimation relating to the bone density from the simple radiation image or the DXA scanning image, in which the learned neural network is learned by using, as teacher data, a composite two-dimensional image representing the subject, which is derived by combining a three-dimensional CT image of the subject, and information relating to the bone density of the subject.

Note that the estimation method according to the present disclosure may be provided as a program causing a computer to execute.

According to the present disclosure, it is possible to estimate the bone density with high accuracy.

DETAILED DESCRIPTION

Figure 1:
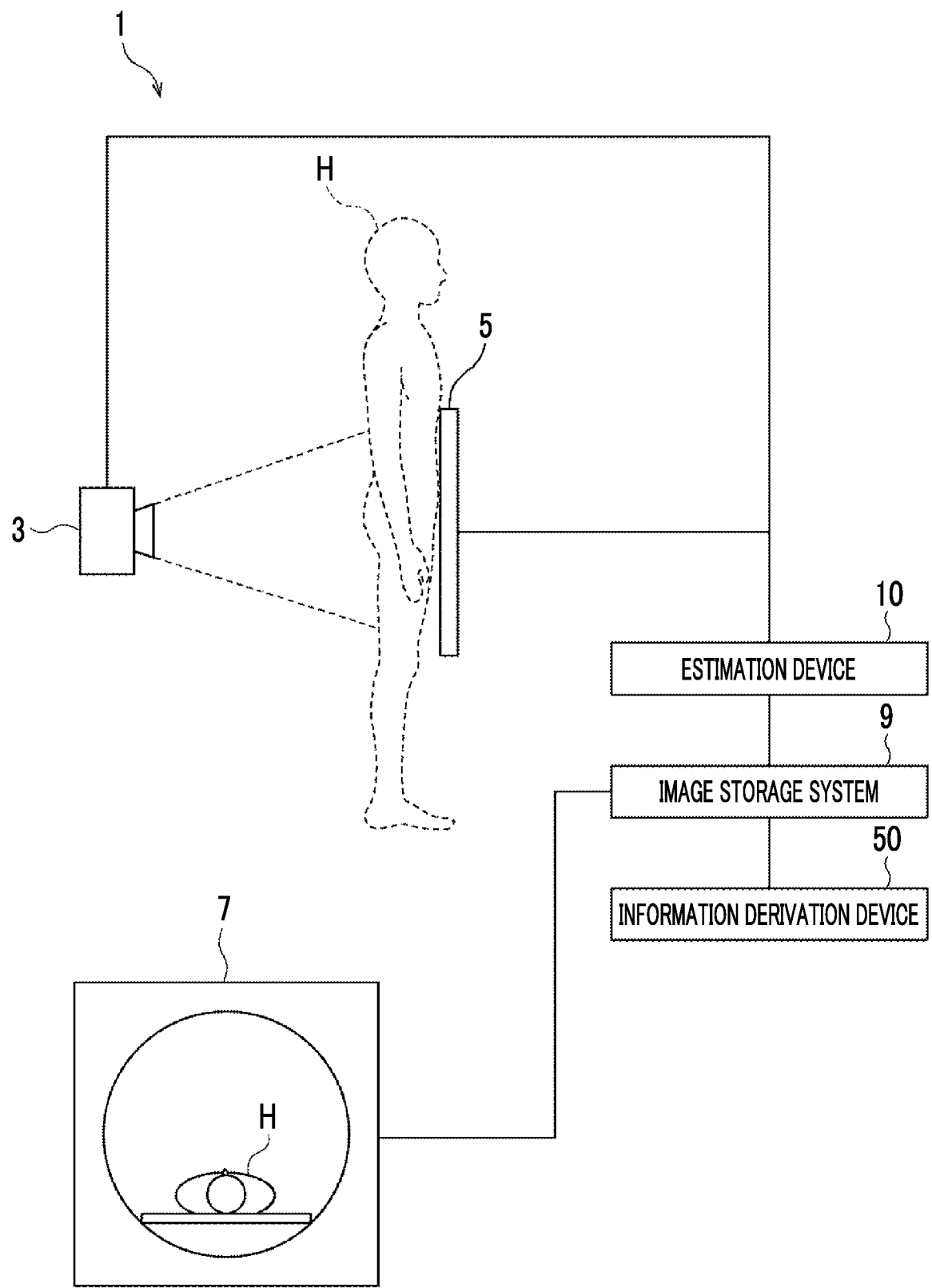
FIG. 1 is a schematic block diagram showing a configuration of a radiography system to which an estimation device according to a first embodiment of the present disclosure is applied.

Hereinafter, embodiments of the present disclosure will be described with reference to the drawings. FIG. 1 is a schematic block diagram showing a configuration of a radiography system to which an estimation device according to a first embodiment of the present disclosure is applied. As shown in FIG. 1, the radiography system according to the first embodiment comprises an imaging apparatus 1, a computed tomography (CT) device 7, an image storage system 9, an estimation device 10 according to the first embodiment, and an information derivation device 50. The imaging apparatus 1, the CT device 7, the estimation device 10, and the information derivation device 50 are connected to the image storage system 9 via a network (not shown).

The imaging apparatus 1 is an imaging apparatus capable of acquiring a simple radiation image G0 of a subject H by irradiating the radiation detector 5 with radiation, such as X-rays, emitted from the radiation source 3 and transmitted through the subject H. The acquired simple radiation image G0 is input to the estimation device 10. The simple radiation image G0 is, for example, a front image including the vicinity of the crotch of the subject H.

The radiation detector 5 can perform recording and reading-out of the radiation image repeatedly. A so-called direct-type radiation detector that directly receives emission of the radiation and generates an electric charge may be used, or a so-called indirect-type radiation detector that converts the radiation into visible light and then converts the visible light into an electric charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

The CT device 7 acquires a plurality of tomographic images representing a plurality of tomographic surfaces of the subject H as a three-dimensional CT image V0. The CT value of each pixel (voxel) in the CT image is a numerical value of the radiation absorbance in the composition constituting the human body. The CT value will be described below.

The image storage system 9 is a system that stores the image data of the radiation image acquired by the imaging apparatus 1 and the image data of the CT image acquired by the CT device 7. The image storage system 9 extracts an image corresponding to requests from the estimation device 10 and the information derivation device 50 from the stored radiation image and CT image and transmits the extracted image to a request source device. Specific examples of the image storage system 9 include picture archiving and communication systems (PACS). Note that in the present embodiment, the image storage system 9 stores a large amount of teacher data for learning the neural network described below.

Figure 2:
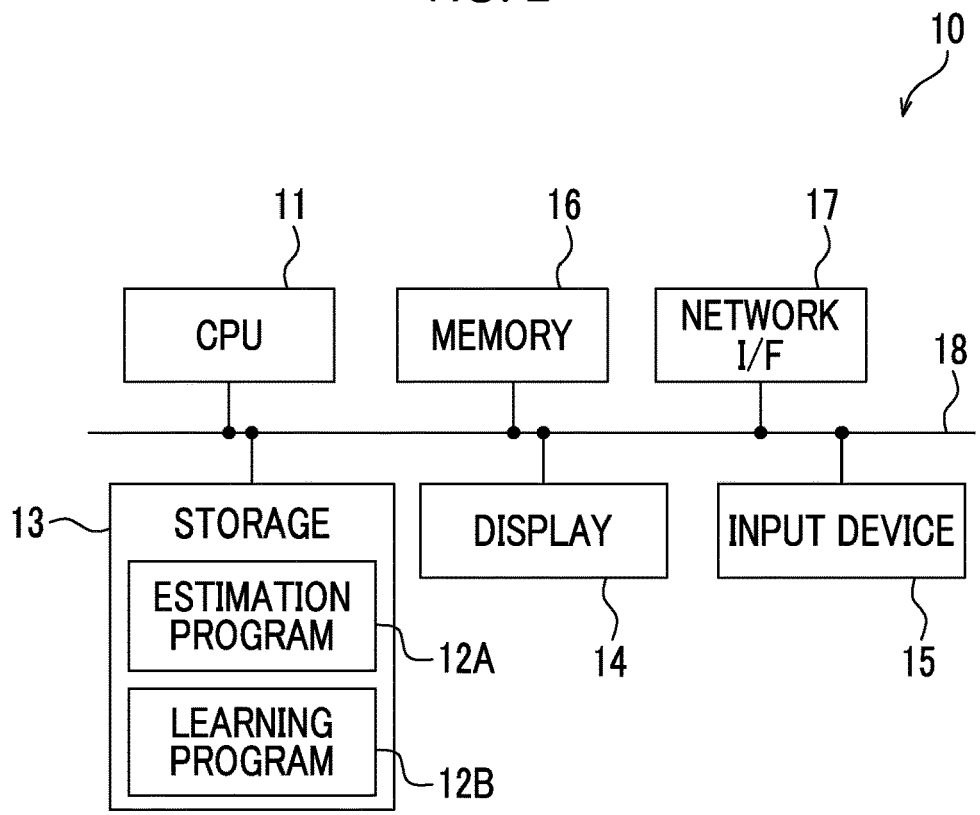
FIG. 2 is a diagram showing a schematic configuration of the estimation device according to the first embodiment.

Then, the estimation device according to the first embodiment will be described. First, a hardware configuration of the estimation device according to the first embodiment will be described with reference to FIG. 2. As shown in FIG. 2, the estimation device 10 is a computer, such as a workstation, a server computer, and a personal computer, and comprises a central processing unit (CPU) 11, a non-volatile storage 13, and a memory 16 as a transitory storage region. In addition, the estimation device 10 comprises a display 14, such as a liquid crystal display, an input device 15, such as a keyboard and a mouse, and a network interface (I/F) 17 connected to a network (not shown). The CPU 11, the storage 13, the display 14, the input device 15, the memory 16, and the network I/F 17 are connected to a bus 18. Note that the CPU 11 is an example of a processor according to the present disclosure.

The storage 13 is realized by a hard disk drive (HDD), a solid state drive (SSD), a flash memory, and the like. The storage 13 as a storage medium stores an estimation program 12A and a learning program 12B installed in the estimation device 10. The CPU 11 reads out the estimation program 12A and the learning program 12B from the storage 13, expands the estimation program 12A and the learning program 12B in the memory 16, and executes the expanded estimation program 12A and the expanded learning program 12B.

Note that the estimation program 12A and the learning program 12B are stored in a storage device of the server computer connected to the network or in a network storage in a state of being accessible from the outside, and are downloaded and installed in the computer that configures the estimation device 10 in response to the request. Alternatively, the estimation program 12A and the learning program 12B are distributed in a state of being recorded on a recording medium, such as a digital versatile disc (DVD) or a compact disc read only memory (CD-ROM), and are installed in the computer that configures the estimation device 10 from the recording medium.

Figure 3:
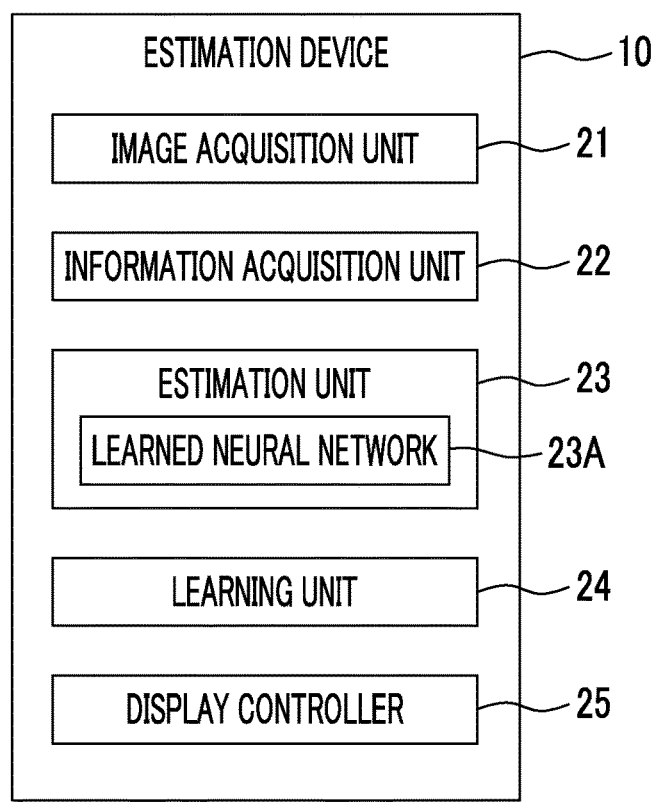
FIG. 3 is a diagram showing a functional configuration of an estimation device according to the first embodiment.

Then, a functional configuration of the estimation device according to the first embodiment will be described. FIG. 3 is a diagram showing the functional configuration of the estimation device according to the first embodiment. As shown in FIG. 3, the estimation device 10 comprises an image acquisition unit 21, an information acquisition unit 22, an estimation unit 23, a learning unit 24, and a display controller 25. Further, the CPU 11 functions as the image acquisition unit 21, the information acquisition unit 22, the estimation unit 23, and the display controller 25 by executing the estimation program 12A. In addition, the CPU 11 functions as the learning unit 24 by executing the learning program 12B.

The image acquisition unit 21 acquires the simple radiation image G0 which is the front image of the vicinity of the crotch of the subject H from the radiation detector 5 by causing the imaging apparatus 1 to perform the simple imaging of the subject H. In a case in which the simple radiation image G0 are acquired, an imaging conditions, such as an imaging dose, a radiation quality, a tube voltage, a source image receptor distance (SID) which is a distance between the radiation source 3 and the surface of the radiation detector 5, a source object distance (SOD) which is a distance between the radiation source 3 and a surface of the subject H, and the presence or absence of a scattered ray removal grid are set.

The imaging conditions need only be set by input from the input device 15 by an operator. The set imaging conditions are stored in the storage 13. The simple radiation image G0 and the imaging conditions are also transmitted to and stored in the image storage system 9.

Note that in the present embodiment, the simple radiation image G0 may be acquired by a program separate from the estimation program 12A and stored in the storage 13. In this case, the image acquisition unit 21 acquires the simple radiation image G0 stored in the storage 13 by reading out the simple radiation image G0 from the storage 13 for processing.

The information acquisition unit 22 acquires the teacher data for learning a neural network, which will be described below, from the image storage system 9 via the network I/F 17.

The estimation unit 23 derives the result of estimation relating to the bone density of the bone part included in the subject H from the simple radiation image G0. In the present embodiment, the result of estimation of the bone density of a target bone in a bone region included in the simple radiation image G0 is derived as the result of estimation of the bone density. Therefore, the estimation unit 23 derives the result of estimation relating to the bone density by using a learned neural network 23A that outputs the bone density in a case in which the simple radiation image G0 is input.

The learning unit 24 constructs the learned neural network 23A by machine learning the neural network by using the teacher data. Examples of the neural network include a simple perceptron, a multi-layer perceptron, a deep neural network, a convolutional neural network, a deep belief network, a recurrent neural network, and a stochastic neural network. In the present embodiment, the convolutional neural network is used as the neural network.

Figure 4:
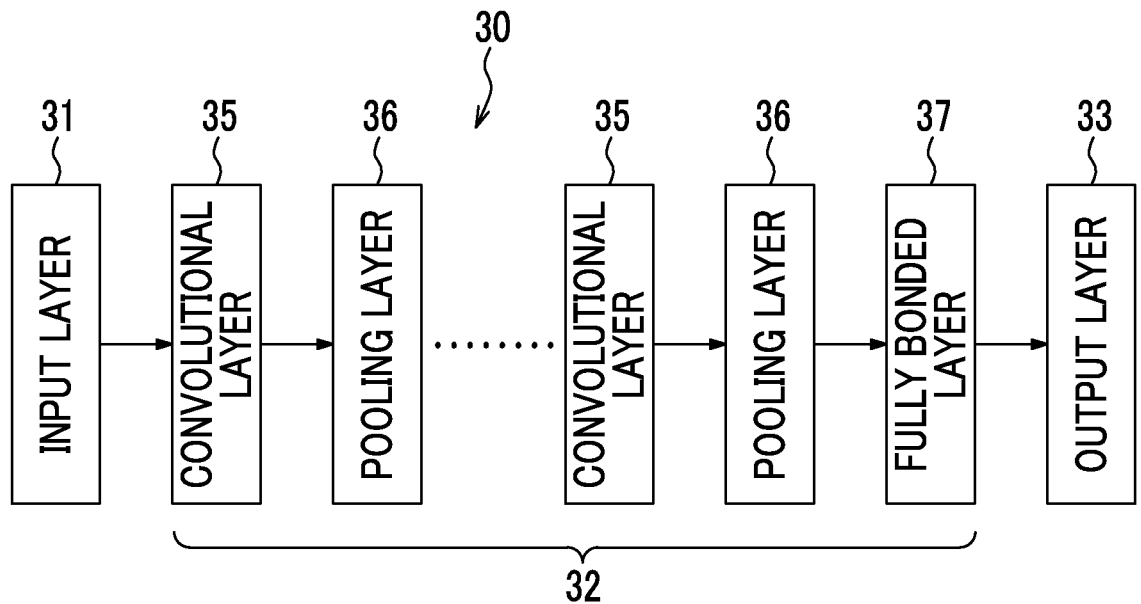
FIG. 4 is a diagram showing a schematic configuration of a neural network used in the present embodiment.

FIG. 4 is a diagram showing the neural network used in the present embodiment. As shown in FIG. 4, a neural network 30 comprises an input layer 31, an interlayer 32, and an output layer 33. The interlayer 32 comprises, for example, a plurality of convolutional layers 35, a plurality of pooling layers 36, and a fully bonded layer 37. In the neural network 30, the fully bonded layer 37 is present in front of the output layer 33. Further, in the neural network 30, the convolutional layer 35 and the pooling layer 36 are alternately disposed between the input layer 31 and the fully bonded layer 37.

Note that a configuration of the neural network 30 is not limited to the example of FIG. 4. For example, the neural network 30 may comprise one convolutional layer 35 and one pooling layer 36 between the input layer 31 and the fully bonded layer 37.

Figure 5:
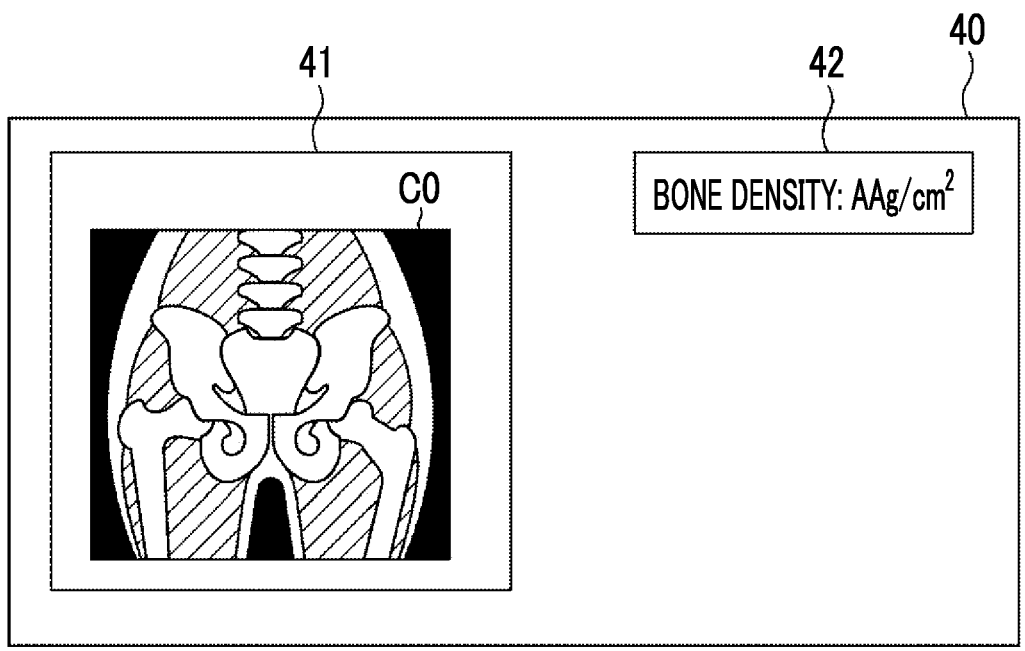
FIG. 5 is a diagram showing teacher data.

FIG. 5 is a diagram showing an example of the teacher data used for learning the neural network. As shown in FIG. 5, teacher data 40 consists of learning data 41 and correct answer data 42. In the present embodiment, the data input to the learned neural network 23A to obtain the result of estimation of the bone density is the simple radiation image G0, but the learning data 41 includes a composite two-dimensional image C0 representing the subject H derived by combining the CT image V0.

The correct answer data 42 is the bone density of the target bone (that is, a femur) of the subject from which the learning data 41 is acquired. Note that in the present embodiment, since the bone density per unit area is estimated from the two-dimensional simple radiation image G0, the unit of the bone density is (g/cm²). The composite two-dimensional image C0, which is the learning data 41, and the bone density, which is the correct answer data 42, are derived by the information derivation device 50. Note that the bone density, which is the correct answer data 42, is an example of information relating to the bone density of the bone part of the subject. Hereinafter, the information derivation device 50 will be described.

Figure 6:
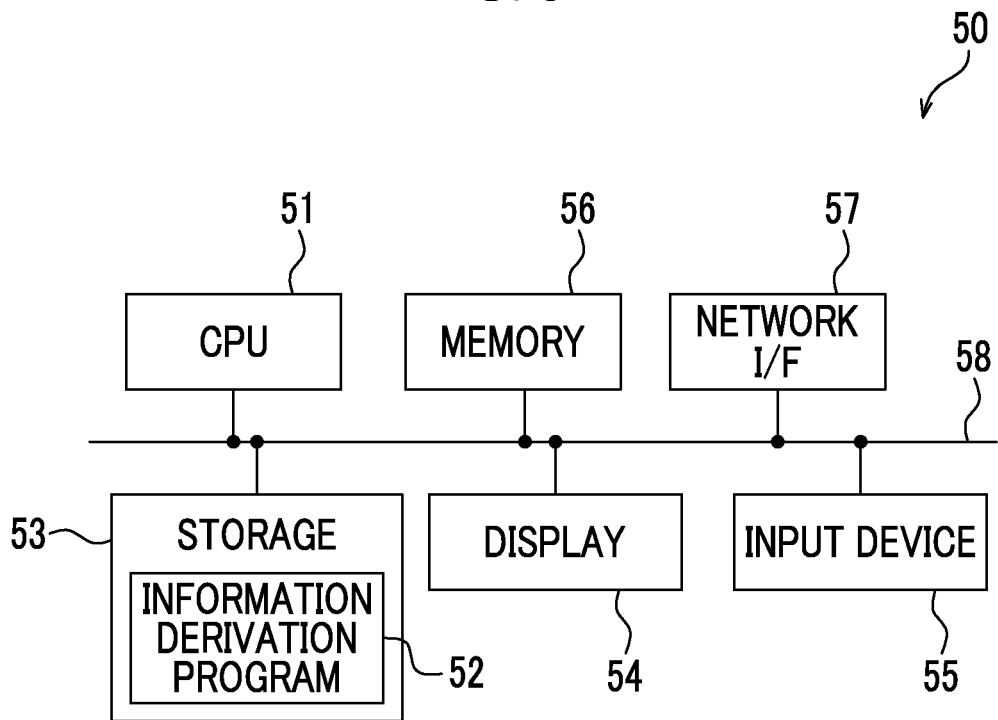
FIG. 6 is a diagram showing a schematic configuration of an information derivation device according to the first embodiment.

FIG. 6 is a schematic block diagram showing a configuration of the information derivation device according to the first embodiment. As shown in FIG. 6, the information derivation device 50 according to the first embodiment is a computer, such as a workstation, a server computer, and a personal computer, and includes a CPU 51, a non-volatile storage 53, and a memory 56 as a transitory storage region. In addition, the information derivation device 50 includes a display 54, such as a liquid crystal display, an input device 55 including a pointing device, such as a keyboard and a mouse, and a network I/F 57 connected to a network (not shown). The CPU 51, the storage 53, the display 54, the input device 55, the memory 56, and the network I/F 57 are connected to a bus 58.

Similar to the storage 13, the storage 53 is realized by the HDD, the SSD, the flash memory, and the like. An information derivation program 52 is stored in the storage 53 as the storage medium. The CPU 51 reads out the information derivation program 52 from the storage 53, expands the read out information derivation program 52 in the memory 56, and executes the expanded information derivation program 52.

Figure 7:
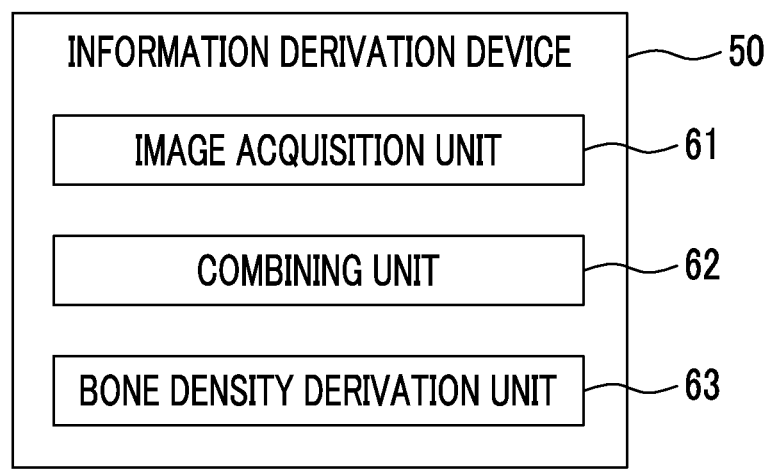
FIG. 7 is a diagram showing a functional configuration of the information derivation device according to the first embodiment.

Then, a functional configuration of the information derivation device according to the first embodiment will be described. FIG. 7 is a diagram showing the functional configuration of the information derivation device according to the first embodiment. As shown in FIG. 7, the information derivation device 50 according to the first embodiment comprises an image acquisition unit 61, a combining unit 62, and a bone density derivation unit 63. Further, the CPU 51 executes the information derivation program 52, so that the CPU 51 functions as the image acquisition unit 61, the combining unit 62, and the bone density derivation unit 63.

The image acquisition unit 61 acquires, from the image storage system 9, the CT image V0 for deriving the learning data 41. The image acquisition unit 61 may acquire the CT image V0 by causing the CT device 7 to image the subject H in the same manner as the image acquisition unit 21 of the estimation device 10.

Figure 8:
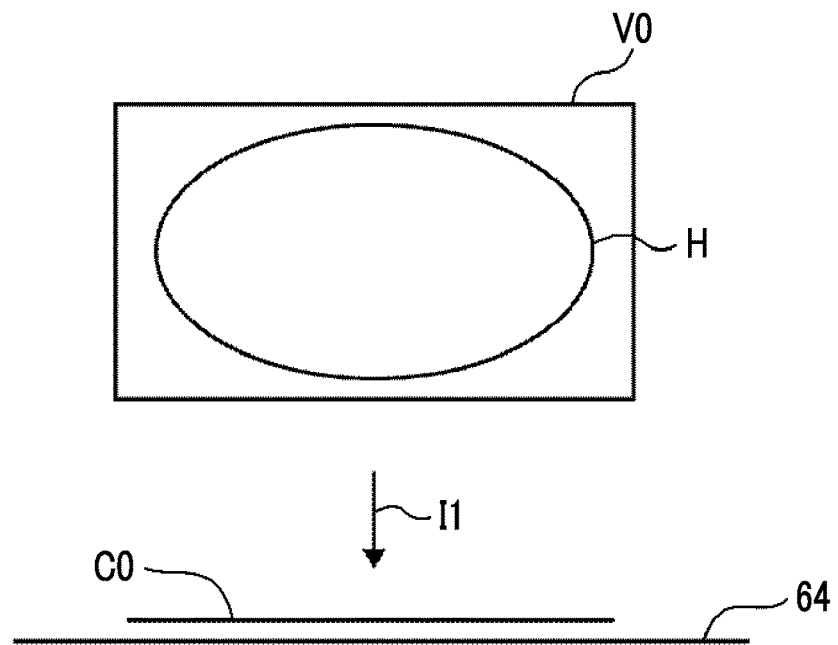
FIG. 8 is a diagram for describing derivation of a composite two-dimensional image.

The combining unit 62 derives the composite two-dimensional image C0 representing the subject H by combining the CT image V0. FIG. 8 is a diagram for describing derivation of the composite two-dimensional image C0. Note that in FIG. 8, the three-dimensional CT image V0 is shown in two dimensions for the sake of description. As shown in FIG. 8, the subject H is included in a three-dimensional space represented by the CT image V0. The subject H includes a plurality of compositions of the bone part, the fat, the muscle, and the internal organs.

Here, the CT value $V0(x,y,z)$ in each pixel of the CT image V0 can be represented by Expression (1) by using an attenuation coefficient $\mu i$ of the composition in the pixel and an attenuation coefficient $\mu w$ of water. (x,y,z) are coordinates representing pixel positions of the CT image V0. Note that, in the following description, the attenuation coefficient means the linear attenuation coefficient unless otherwise specified. The attenuation coefficient represents a degree (ratio) of the radiation attenuation due to absorption or scattering. The attenuation coefficient differs depending on a specific composition (density or the like) and the thickness (mass) of the structure through which radiation is transmitted.

$$V0(x,y,z)=(\mu i-\mu w)/\mu w \times 1000 \qquad (1)$$

The attenuation coefficient $\mu w$ of the water is known. Therefore, by solving Expression (1) for $\mu i$, the attenuation coefficient $\mu i$ of each composition can be calculated as shown in Expression (2).

$$\mu i = V0(x,y,z) \times \mu w/1000 + \mu w \qquad (2)$$

As shown in FIG. 8, the combining unit 62 virtually irradiates the subject H with the radiation having an irradiation dose I0, and derives the composite two-dimensional image C0 obtained by virtually detecting the radiation transmitted through the subject H by the radiation detector (not shown) installed on a virtual plane 64. Note that the irradiation dose I0 of the virtual radiation and the radiation energy are set depending on predetermined imaging conditions. Specifically, the radiation dose I0 need only be set by preparing a table corresponding to the imaging conditions, such as the tube voltage, the mAs value, and the SID, and referring to the table. In addition, the radiation energy need only be set by preparing the table depending on the tube voltage and referring to the table. In this case, a reaching dose $I1(x,y)$ for each pixel of the composite two-dimensional image C0 is transmitted through one or more compositions in the subject H. Therefore, the reaching dose $I1(x,y)$ can be derived by Expression (3) by using the attenuation coefficient $\mu i$ of one or more compositions through which the radiation of the irradiation dose I0 is transmitted. Note that the reaching dose $I1(x,y)$ is the pixel value of each pixel of the composite two-dimensional image C0.

$$I1(x,y)=I0 \times \exp(-\int \mu i \cdot dt) \qquad (3)$$

Figure 9:
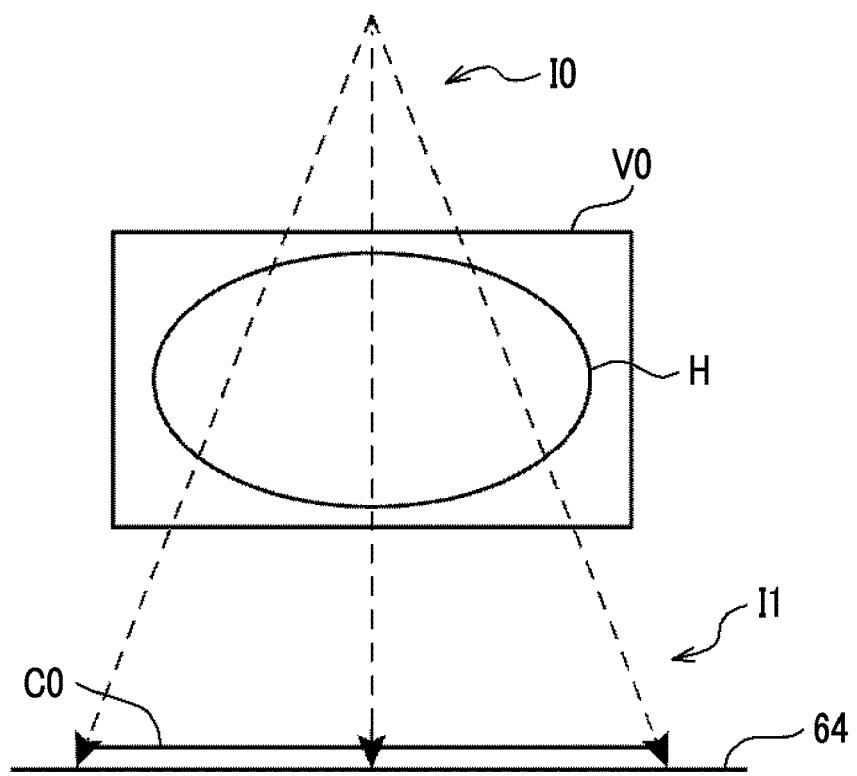
FIG. 9 is a diagram for describing the derivation of the composite two-dimensional image.

Note that in a case in which it is assumed that the radiation source to be irradiated is a plane light source, as the attenuation coefficient $\mu i$ used in Expression (3), a value derived from the CT value of the pixels arranged in the vertical direction shown in FIG. 8 by Expression (2) need only be used. In addition, in a case in which it is assumed that the plane light source of the light source to be emitted is a point light source, as shown in FIG. 9, based on the geometric positional relationship between the point light source and each position on the virtual plane 64, the pixel on the path of the radiation reaching each pixel need only be specified and the attenuation coefficient $\mu i$ derived from the CT value of the specified pixel by Expression (2) need only be used.

Figure 10:
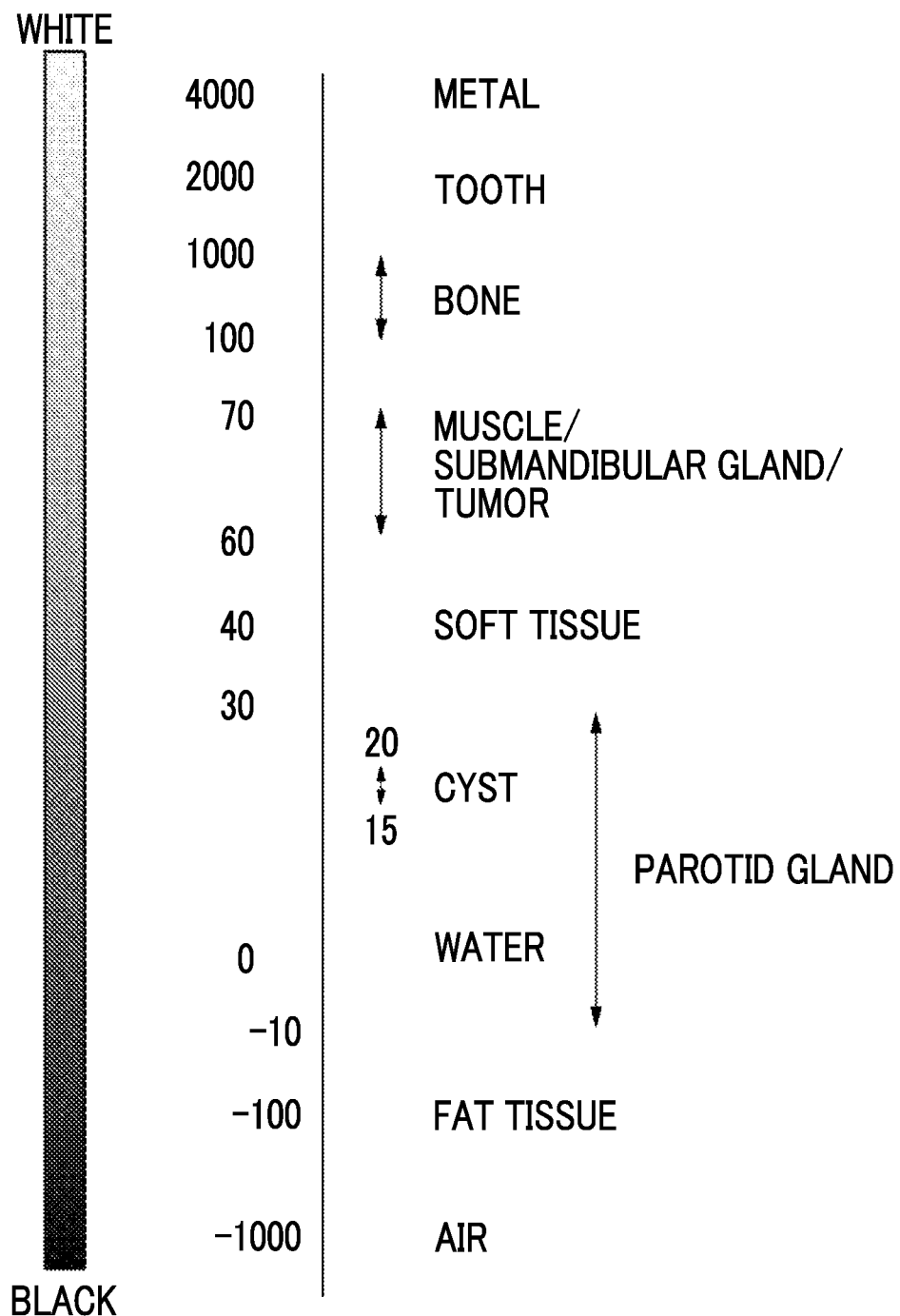
FIG. 10 is a diagram for describing a CT value.

The bone density derivation unit 63 derives the bone density of the subject H for each pixel of the composite two-dimensional image C0 by using the CT image V0. Here, description for the CT value will be made. FIG. 10 is a diagram for describing the CT value. The CT value is a numerical value of the X-ray absorbance in the human body. Specifically, as shown in FIG. 10, the CT value is determined depending on the composition constituting the human body, such as 0 for the water and —1000 (unit: HU) for the air.

The bone density derivation unit 63 first specifies the bone region in the CT image V0 based on the CT value of the CT image V0. Specifically, a region consisting of the pixels having the CT value of 100 to 1000 is specified as the bone region by threshold value processing. Note that the bone region may be specified by using the learned neural network learned to detect the bone region from the CT image V0 instead of the threshold value processing. In addition, the bone region may be specified by displaying the CT image V0 on the display 54 and receiving designation of the bone region by a manual operation in the displayed CT image V0.

Here, the density ρ [g/cm$^3$] per unit volume of the composition in each pixel of the CT image can be derived by Expression (4) from the attenuation coefficient μi [1/cm] of the composition and the mass attenuation coefficient μe [cm$^2$/g] of the composition.

$$\rho = \mu i / \mu e \quad (4)$$

Figure 11:
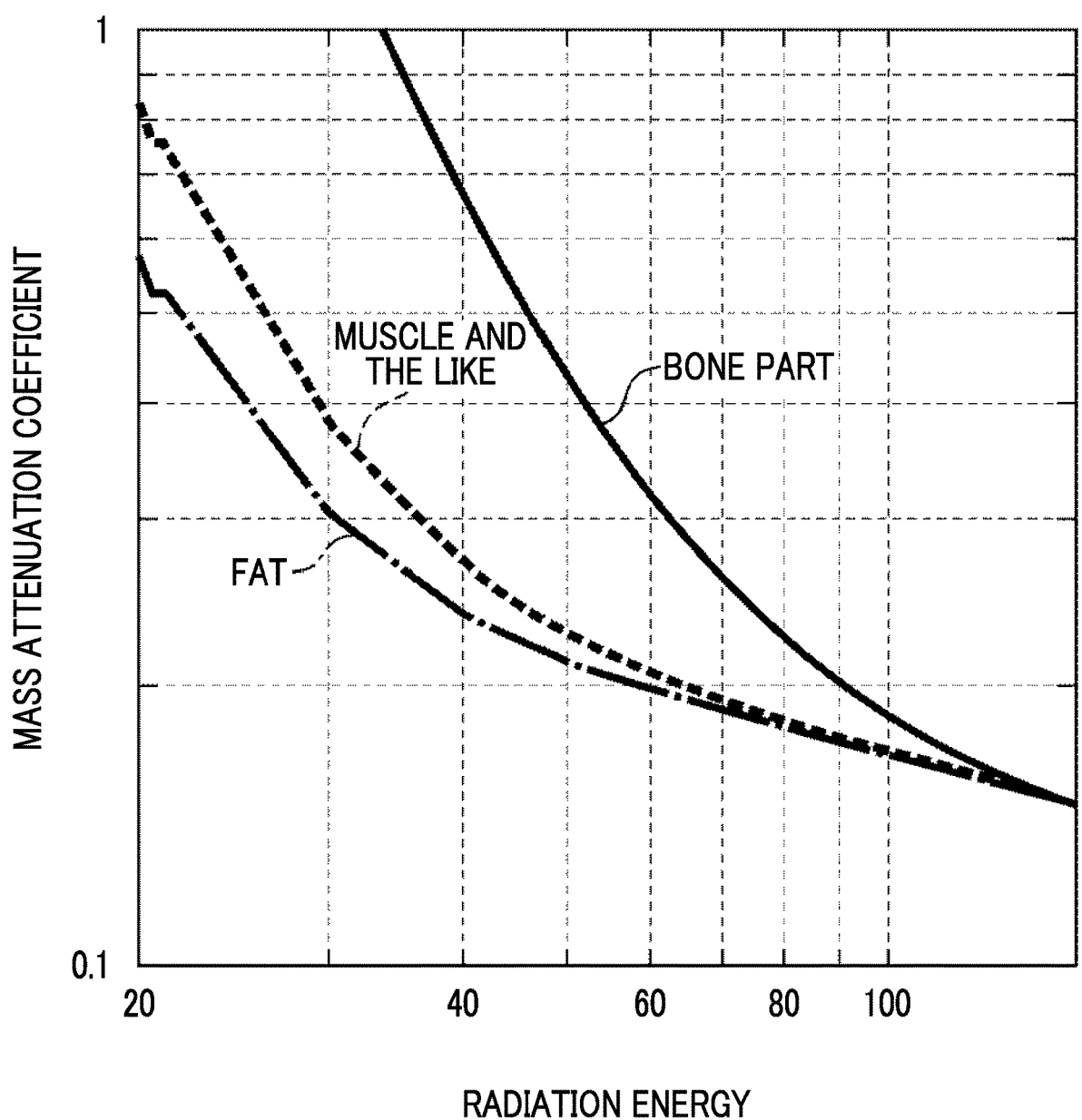
FIG. 11 is a diagram showing a relationship between radiation energy and a mass attenuation coefficient.

FIG. 11 is a diagram showing a relationship between the radiation energy and the mass attenuation coefficient in various compositions of the human body. FIG. 11 shows the relationship between the radiation energy and the mass attenuation coefficient for the bone part, the muscle and the like, and the fat. Note that the muscle and the like mean the muscle, the blood, and the water. In the present embodiment, the relationship between the radiation energy and the mass attenuation coefficient, which is shown in FIG. 11, is stored in the storage 53 as a table. In the present embodiment, since the mass attenuation coefficient of the bone part is required, the mass attenuation coefficient of the bone part is acquired by referring to the relationship of the bone part in the table shown in FIG. 11 based on the virtual radiation energy. In addition, the attenuation coefficient μb in each pixel of the bone region is derived by Expression (2). Further, the bone density ρ per unit volume in each pixel of the bone region included in the CT image V0 is derived by Expression (4).

Note that the CT image V0 is the three-dimensional image, the unit of the bone density per unit volume derived by Expression (4) is [g/cm$^3$]. In the present embodiment, the bone density derivation unit 63 derives the bone density per unit area for each pixel of the composite two-dimensional image C0. Therefore, the bone density derivation unit 63 projects the bone density ρ per unit volume derived by Expression (4) onto the virtual plane 64 in the same manner as a case in which the composite two-dimensional image C0 is derived to derive the bone density B [g/cm$^2$] per unit area for each pixel of the composite two-dimensional image C0.

Note that in a case of projection, a representative value of the bone density of each pixel of the CT image V0 on the path reaching each pixel of the composite two-dimensional image C0 from the virtual radiation source need only be derived. An integrated value, an average value, a maximum value, a median value, a minimum value, and the like can be used as the representative value. Moreover, in the present embodiment, the bone density derivation unit 63 need only derive the representative value of bone density for the target bone. For example, in a case in which the target bone is the femur, the bone density derivation unit 63 derives the representative value of the bone density of the femur region by deriving the representative value of the bone density of each pixel in the femur region in the composite two-dimensional image C0. An average value, a median value, a minimum value, a maximum value, and the like can be used as the representative value. In the present embodiment, the representative value of the bone density of the femur, which is the target bone, is used as the correct answer data 42.

The bone density, which is used as the correct answer data 42, is derived at the same time as the time when the learning data 41 is acquired, and is transmitted to the image storage system 9. In the image storage system 9, the learning data 41 and the correct answer data 42 are stored in association with each other as the teacher data 40. Note that in order to improve the robustness of the learning, the teacher data 40 including, as learning data 41, an image obtained by performing at least one of enlargement/reduction, contrast change, movement, in-plane rotation, inversion, or noise addition on the same image may be additionally created and stored.

Figure 12:
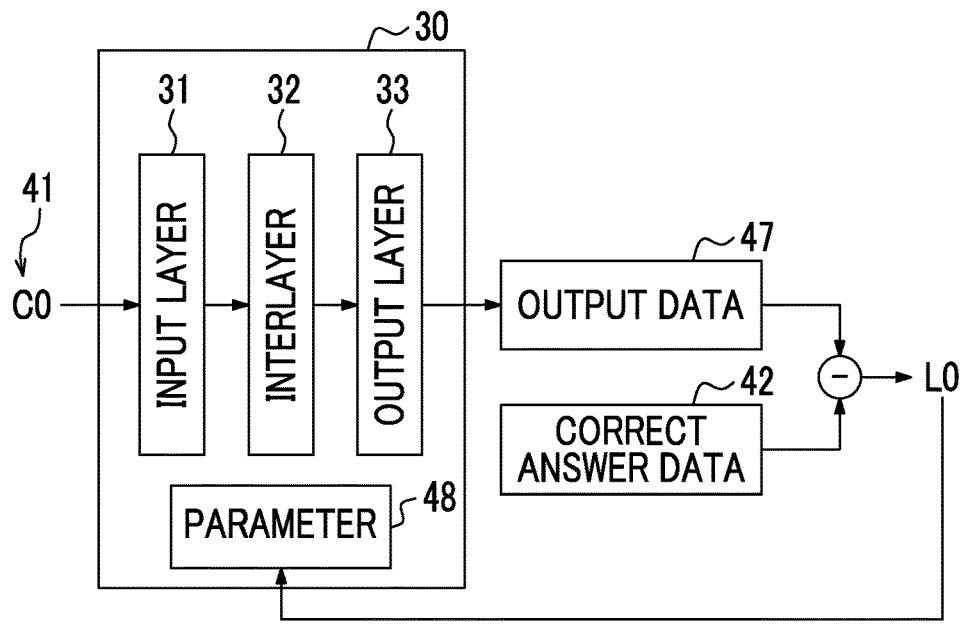
FIG. 12 is a diagram for describing learning of the neural network.

The description will be returned to the estimation device 10. The learning unit 24 learns the neural network by using a large amount of the teacher data 40. FIG. 12 is a diagram for describing learning of the neural network 30. In a case in which the neural network 30 is learned, the learning unit 24 inputs the learning data 41, that is, the composite two-dimensional image C0 to the input layer 31 of the neural network 30. Further, the learning unit 24 outputs the bone density of the target bone as output data 47 from the output layer 33 of the neural network 30. Further, the learning unit 24 derives a difference between the output data 47 and the correct answer data 42 as a loss L0.

The learning unit 24 learns the neural network 30 based on the loss L0. Specifically, the learning unit 24 adjusts a kernel coefficient in the convolutional layer 35, a weight of the bond between the layers, a weight of the bond in the fully bonded layer 37, and the like (hereinafter referred to as a parameter 48) such that the loss L0 is reduced. For example, an error backpropagation method can be used as a method for adjusting the parameter 48. The learning unit 24 repeats the adjustment of the parameter 48 until the loss L0 is equal to or smaller than a predetermined threshold value. As a result, in a case in which the simple radiation image G0 is input, the parameter 48 is adjusted so as to output the bone density of the target bone, and the learned neural network 23A is constructed. The constructed learned neural network 23A is stored in the storage 13.

Figure 13:
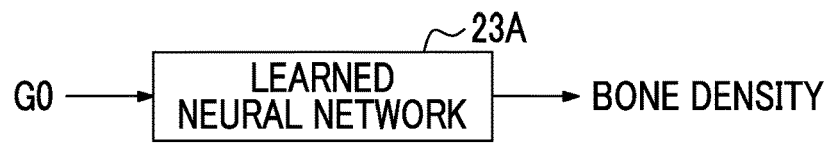
FIG. 13 is a conceptual diagram of processing performed by a learned neural network.

FIG. 13 is a conceptual diagram of processing performed by the learned neural network 23A. As shown in FIG. 13, in a case in which the simple radiation image G0 of a patient is input to the learned neural network 23A constructed as described above, the learned neural network 23A outputs the bone density for the target bone (that is, the femur) included in the input simple radiation image G0.

Figure 14:
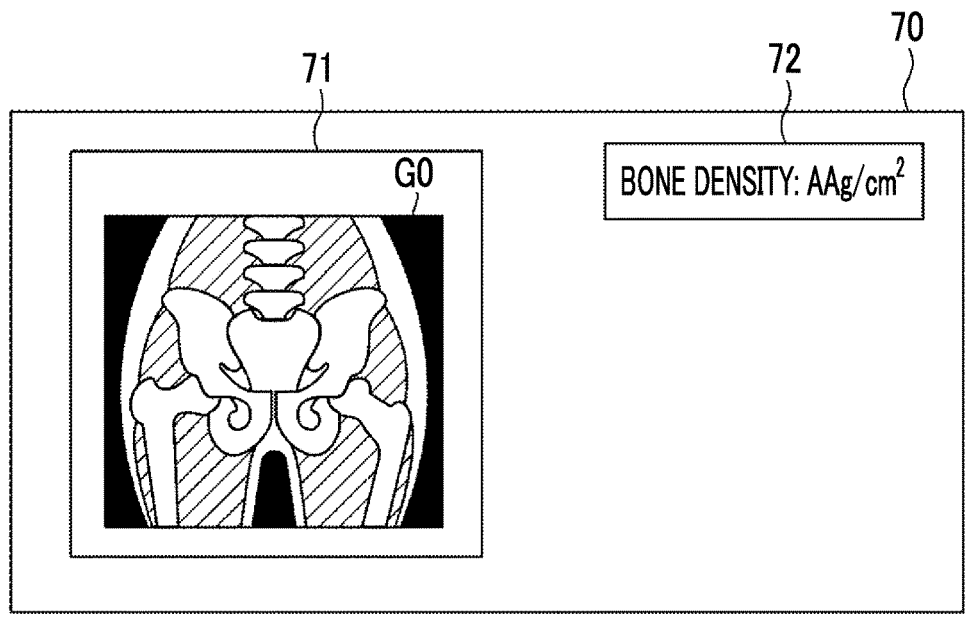
FIG. 14 is a diagram showing a display screen of a result of estimation.

The display controller 25 displays the result of estimation of the bone density estimated by the estimation unit 23 on the display 14. FIG. 14 is a diagram showing a display screen of the result of estimation. As shown in FIG. 14, a display screen 70 has an image display region 71 and a bone density display region 72. The simple radiation image G0 of the subject H is displayed in the image display region 71. In addition, in the bone density display region 72, the representative value of the bone density in the vicinity of the joint of the femur in the bone density estimated by the estimation unit 23 is displayed.

Figure 15:
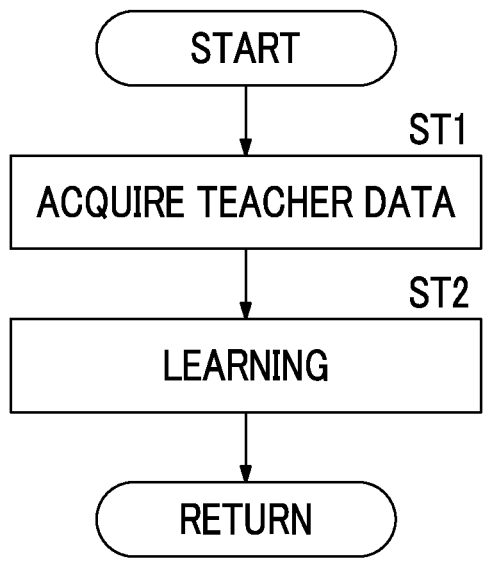
FIG. 15 is a flowchart of learning processing performed in the first embodiment.

Then, the processing performed in the first embodiment will be described. FIG. 15 is a flowchart showing learning processing performed in the first embodiment. First, the information acquisition unit 22 acquires the teacher data 40 from the image storage system 9 (step ST1), and the learning unit 24 inputs the learning data 41 included in the teacher data 40 to the neural network 30 to output the bone density and learns the neural network 30 by using the loss L0 based on the difference from the correct answer data 42 (step ST2), and the processing returns to step ST1. Further, the learning unit 24 repeats the processing of steps ST1 and ST2 until the loss L0 reaches the predetermined threshold value, and terminates the learning processing. Note that the learning unit 24 may terminate the learning processing by repeating the learning a predetermined number of times. As a result, the learning unit 24 constructs the learned neural network 23A.

Figure 16:
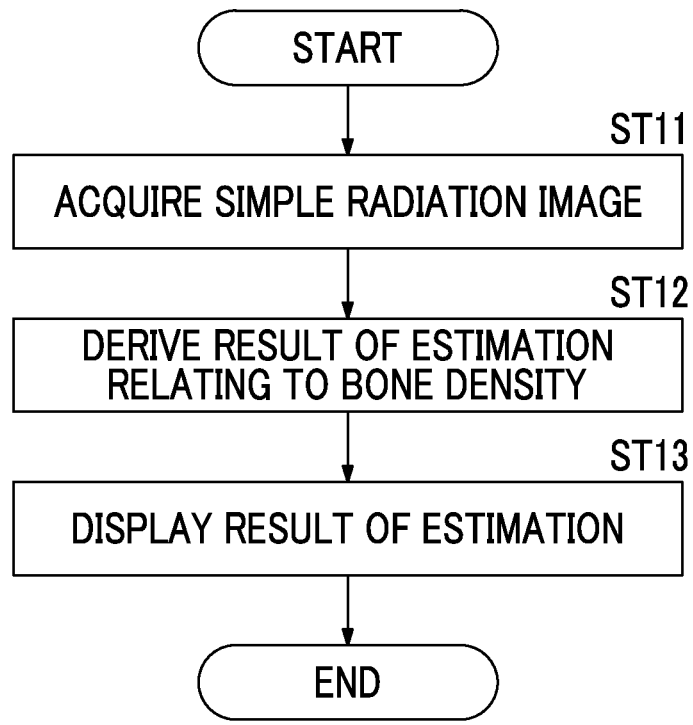
FIG. 16 is a flowchart showing estimation processing performed in the first embodiment.

Then, estimation processing in the first embodiment will be described. FIG. 16 is a flowchart showing the estimation processing in the first embodiment. Note that the simple radiation image G0 is acquired by the imaging and stored in the storage 13. In a case in which an instruction for starting the processing is input from the input device 15, the image acquisition unit 21 acquires the simple radiation image G0 from the storage 13 (step ST11). Then, the estimation unit 23 derives the result of estimation relating to the bone density from the simple radiation image G0 (step ST12). Further, the display controller 25 displays the result of estimation relating to the bone density derived by the estimation unit 23 on the display 14 together with the simple radiation image G0 (step ST13), and terminates the processing.

As described above, in the present embodiment, the result of estimation relating to the bone density of the subject H included in the simple radiation image G0 is derived by using the learned neural network 23A constructed by performing learning with the composite two-dimensional image C0 derived from the CT image V0 and the bone density derived from the CT image V0 as teacher data. Here, in the present embodiment, the composite two-dimensional image C0 derived from the CT image V0 and the bone density derived from the CT image V0 are used for learning the neural network. Therefore, the learned neural network 23A can derive the result of estimation relating to the bone density from the simple radiation image G0 with higher accuracy as compared with a case in which one radiation image and the information relating to the bone density derived from the radiation image are used as the teacher data. Therefore, according to the present embodiment, the result of estimation relating to the bone density can be derived with higher accuracy.

Figure 17:
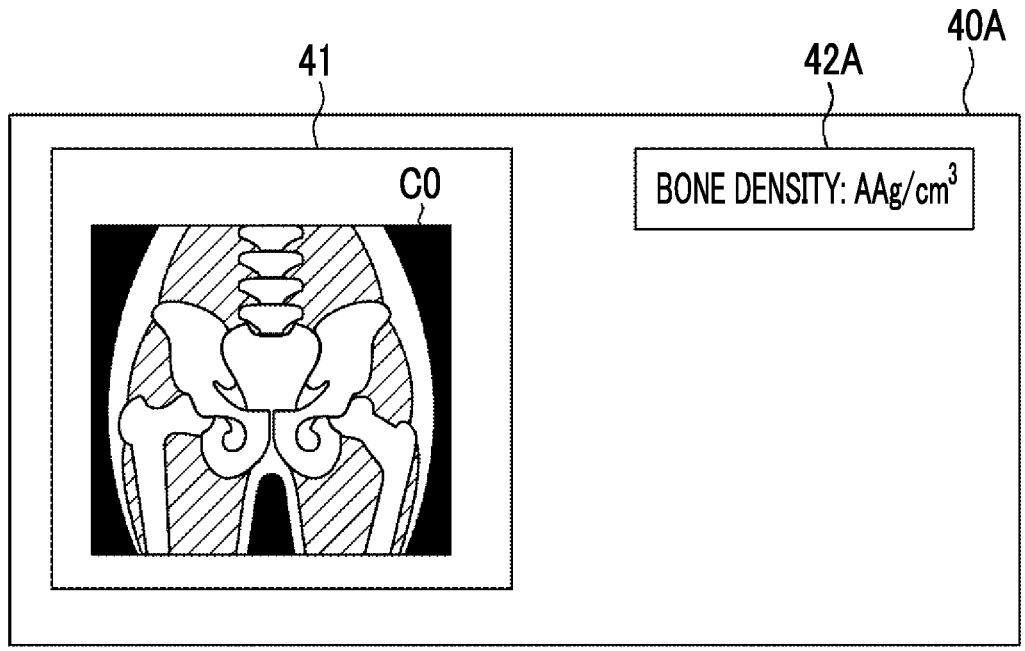
FIG. 17 is a diagram showing another example of the teacher data.

In the first embodiment, the bone density per unit area is derived as the correct answer data 42, but the present disclosure is not limited to this. In the first embodiment, the bone density per unit area may be derived by using, as the correct answer data, the bone density per unit volume obtained in the derivation process. As the bone density per unit volume, the representative value of the bone density in the pixels in the region of the target bone of the CT image V0 need only be used. An average value, a median value, a minimum value, a maximum value, and the like can be used as the representative value. The teacher data in this case is shown in FIG. 17. As shown in FIG. 17, teacher data 40A consists of the learning data 41 including the composite two-dimensional image C0 and correct answer data 42A which is the bone density per unit volume.

By learning the neural network by using the teacher data 40A shown in FIG. 17, it is possible to construct the learned neural network 23A that outputs the bone density per unit volume as the result of estimation relating to the bone density in a case in which the simple radiation image G0 is input.

In addition, in each of the embodiments described above, the bone density per unit area or per unit volume of the simple radiation image G0 is estimated as the information relating to the bone density, but the present disclosure is not limited to this. For example, the evaluation value of the fracture risk may be derived as the result of estimation relating to the bone density. Hereinafter, this case will be described as a second embodiment.

Figure 18:
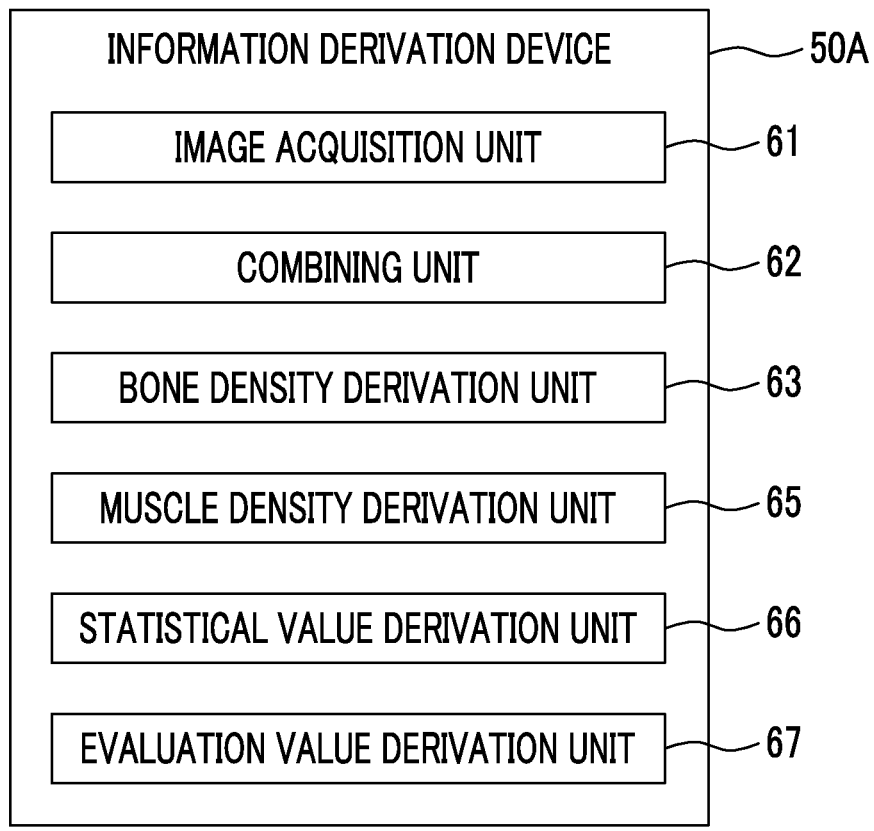
FIG. 18 is a diagram showing a functional configuration of an information derivation device according to a second embodiment.

FIG. 18 is a diagram showing a functional configuration of an information derivation device according to the second embodiment. Note that in FIG. 18, the same reference numerals are assigned to the same configurations as those in FIG. 7, and the detailed description thereof will be omitted.

In the second embodiment of the present disclosure, instead of the derivation of the bone density, the evaluation value of the fracture risk is derived as the correct answer data 42. Therefore, as shown in FIG. 18, an information derivation device 50A according to the second embodiment further comprises a muscle density derivation unit 65, a statistical value derivation unit 66, and an evaluation value derivation unit 67 with respect to the information derivation device 50 according to the first embodiment.

The muscle density derivation unit 65 specifies the muscle region based on the CT value in the CT image V0. Specifically, a region consisting of the pixels having the CT value of 60 to 70 is specified as the muscle region by the threshold value processing. Note that the muscle region may be detected by using the learned neural network learned to detect the muscle region from the CT image V0 instead of the threshold value processing. In addition, the muscle region may be specified by displaying the CT image V0 on the display 54 and receiving designation of the muscle region by the manual operation in the displayed CT image V0.

Further, the muscle density derivation unit 65 calculates an attenuation coefficient $\mu m$ of the muscle by Expression (2). Further, the mass attenuation coefficient of the muscle is acquired by referring to the table shown in FIG. 11. Further, a density pm of the muscle per unit volume is derived from Expression (4).

The statistical value derivation unit 66 obtains a statistical value regarding the subject H based on the bone density derived by the bone density derivation unit 63 and the muscle density derived by the muscle density derivation unit 65. The statistical value is used for calculation of the evaluation value of the fracture risk for evaluating the fracture risk, as will be described below. Specifically, as shown in Expression (5), the statistical value derivation unit 66 derives a statistical value Q based on a bone density distribution index value Bd relating to the spatial distribution of bone density and a muscle mass distribution index value Md relating to the spatial distribution relating to the muscle mass.

$$Q = W1 \times Bd + W2 \times Md \tag{5}$$

W1 and W2 in Expression (5) are weighting coefficients, respectively, and a large amount of the bone density distribution index values and the muscle density distribution index values are collected and determined depending on regression analysis.

The bone density distribution index value is a value representing a spread aspect of the bone density value. Examples of the bone density distribution index value include a value of the bone density per unit area or unit volume, an average value thereof, an intermediate value thereof, a maximum value thereof, a minimum value thereof, and the like. The muscle density distribution index value is a value representing a spread aspect of the muscle density value. Examples of the muscle density distribution index value include a value of the muscle density per unit area or unit volume, an average value thereof, an intermediate value thereof, a maximum value thereof, a minimum value thereof, and the like.

In addition, the statistical value derivation unit 66 may obtain the statistical value Q based on at least one of the height, the weight, the age, or the fracture history of the subject in addition to the bone density and the muscle density. For example, in a case of obtaining the statistical value based on the bone density, the muscle density, and the age, the statistical value Q is calculated by Expression (6)

based on the bone density distribution index value Bd, the muscle mass distribution index value Md, and an age Y.

$$Q = W1 \times Bd + W2 \times Md + W3 \times Y \quad (6)$$

W1, W2, and W3 of Expression (6) are weighting coefficients, respectively, a large amount of data relating to the bone density distribution index value, the muscle density distribution index value, and the age of the subject corresponding to the index values are collected, and the weighting coefficients W1, W2, and W3 are determined based on the regression analysis based on the data. Note that in a case in which the height, the weight, and the fracture history of the subject are added in addition to the age to obtain the statistical value, it is preferable to perform addition by multiplying by the weighting coefficient.

The evaluation value derivation unit 67 calculates the evaluation value of the fracture risk for evaluating the fracture risk of the subject H based on the statistical value Q. Since the relationship between the statistical value Q and the evaluation value of the fracture risk is obtained from a large amount of diagnostic data, the evaluation value derivation unit 67 calculates the evaluation value of the fracture risk using this relationship. The relationship between the statistical value Q and the evaluation value of the fracture risk need only be derived in advance and stored in the storage 53 as a table.

Figure 19:
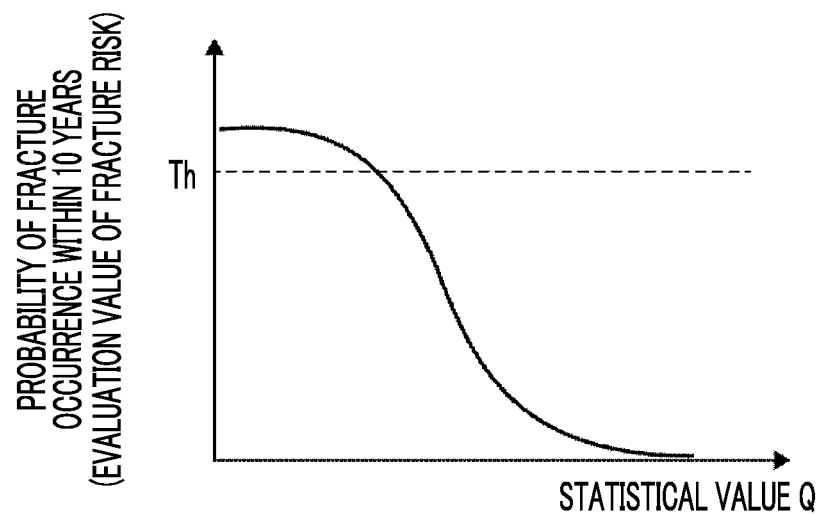
FIG. 19 is a graph showing a relationship between a statistical value and a probability of fracture occurrence within 10 years.

For example, as the evaluation value of the fracture risk, there is a probability of fracture occurrence within 10 years from the time of diagnosis of the subject H (at the time of acquisition of the simple radiation image G0). Further, as described above, in a case in which Expression (6) is used for the calculation of the statistical value Q, the relationship between the "probability of fracture occurrence within 10 years" and the "statistical value Q" is represented such that the probability of fracture occurrence is lower as the statistical value Q is larger, as shown FIG. 19.

Figure 20:
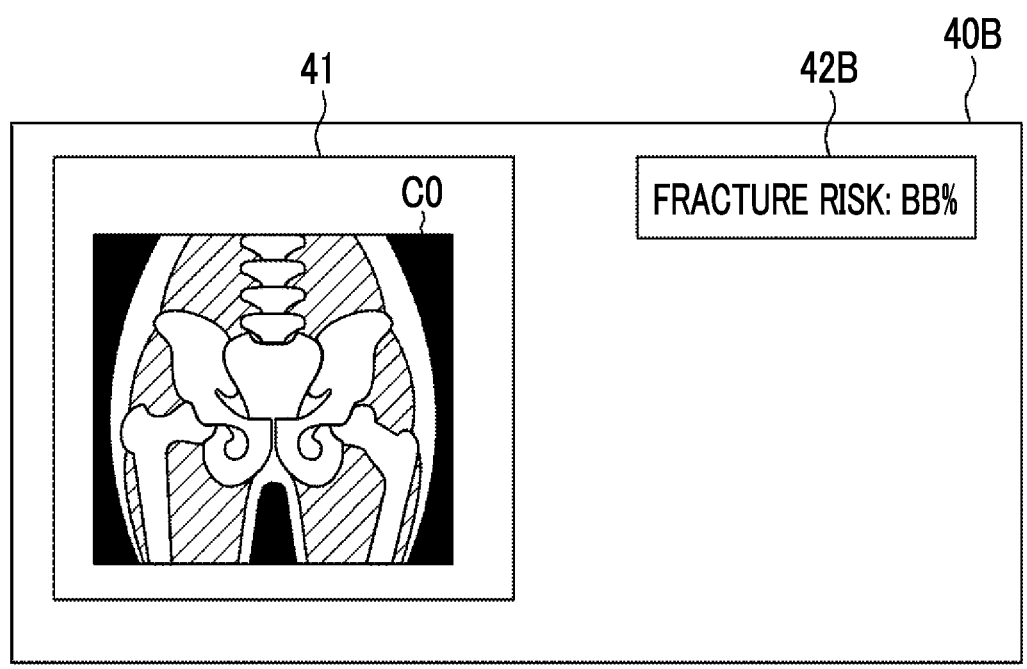
FIG. 20 is a diagram showing still another example of the teacher data.

In the second embodiment, the evaluation value of the fracture risk derived by the information derivation device 50A is used as the correct answer data of the teacher data. FIG. 20 is a diagram showing the teacher data derived in the second embodiment. As shown in FIG. 20, the teacher data 40B consists of the learning data 41 including the composite two-dimensional image C0 and correct answer data 42B which is the evaluation value of the fracture risk.

By learning the neural network by using the teacher data 40B shown in FIG. 20, it is possible to construct the learned neural network 23A that outputs the evaluation value of the fracture risk as the result of estimation relating to the bone density in a case in which the simple radiation image G0 is input.

Figure 21:
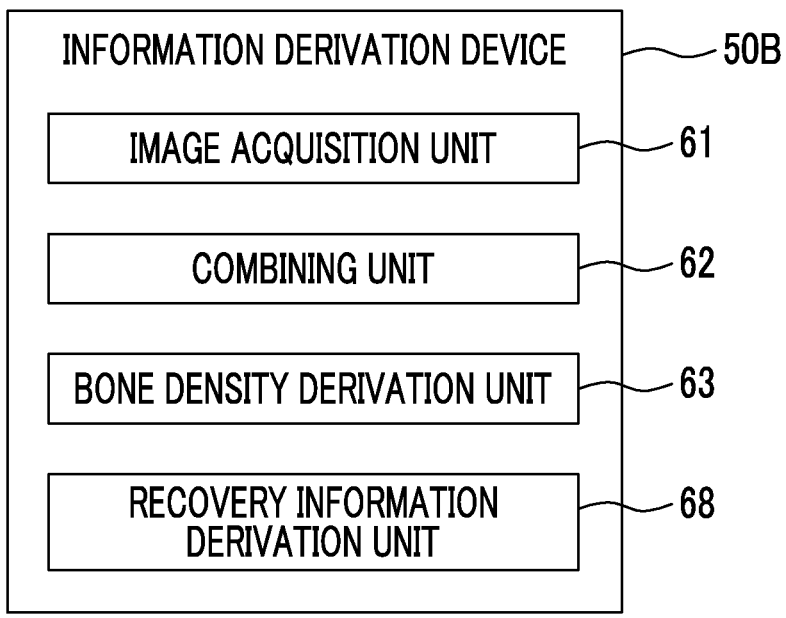
FIG. 21 is a diagram showing a functional configuration of an information derivation device according to a third embodiment.

Then, a third embodiment of the present disclosure will be described. FIG. 21 is a diagram showing a functional configuration of an information derivation device according to the third embodiment. Note that in FIG. 21, the same reference numerals are assigned to the same configurations as those in FIG. 7, and the detailed description thereof will be omitted. In the third embodiment of the present disclosure, instead of deriving the bone density, information representing a recovery state of the bone part after a treatment is derived as the correct answer data 42. Therefore, as shown in FIG. 21, an information derivation device 50B according to the third embodiment further comprises a recovery information derivation unit 68 with respect to the information derivation device 50 according to the first embodiment. Note that in the third embodiment, as the treatment for the bone part, a surgery for embedding an artificial material, such as an artificial bone, in the bone part is performed.

The recovery information derivation unit 68 derives the information representing a state of the bone part of the subject after the artificial material is embedded in the bone part of the subject H as the recovery information based on the bone density in the vicinity of the artificial material, such as the artificial bone, embedded in the bone part of the subject H. The artificial material, such as the artificial bone, is surgically embedded in the living body to replace bone lost due to pulverization fracture, tumor, or the like.

Figure 22:
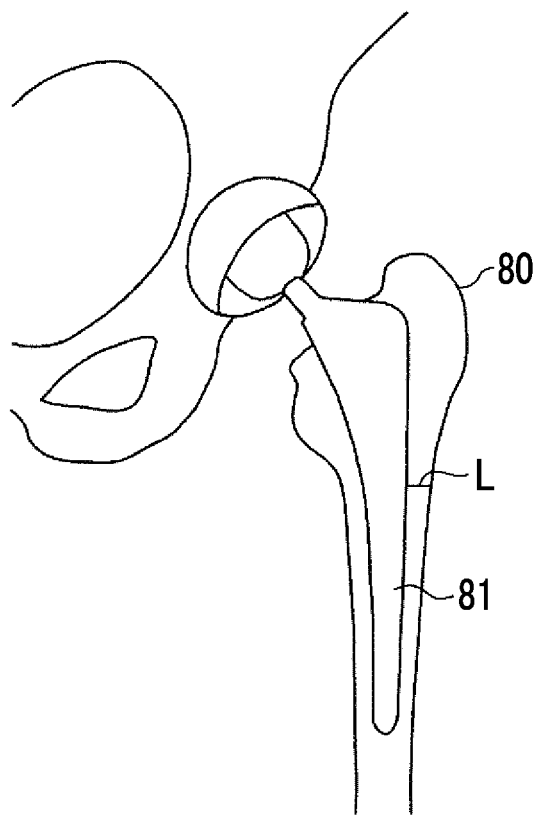
FIG. 22 is a diagram showing an example of an artificial bone embedded in the bone part of the subject.

FIG. 22 is a diagram showing an example of the artificial bone embedded in the bone part of the subject. FIG. 22 shows the bone part of the subject H that subjected to total hip joint replacement therapy, and a stem 81 of the artificial joint is embedded in a femur 80 of the subject H.

As a method for fixing the stem 81, a direct fixation method (cementless fixation) and an indirect fixation method (cement fixation) are known. In the direct fixation method, the stem 81 is inserted into an internal cavity of the femur 80 without the use of cement. The internal cavity of the femur 80 is shaped in advance to fit the stem 81. A surface of the stem 81 is roughened, and the bone tissue grows so as to permeate the inside of the stem 81. That is, immediately after embedding the stem 81 in the femur 80, the cavity is present between the stem 81 and the femur 80, but in a case in which the femur 80 is recovered, the cavity shrinks and disappears as the bone tissue grows. Therefore, by acquiring the bone density in the vicinity of the stem 81, it is possible to grasp the degree of recovery of the femur 80 after the surgery.

Figure 23:
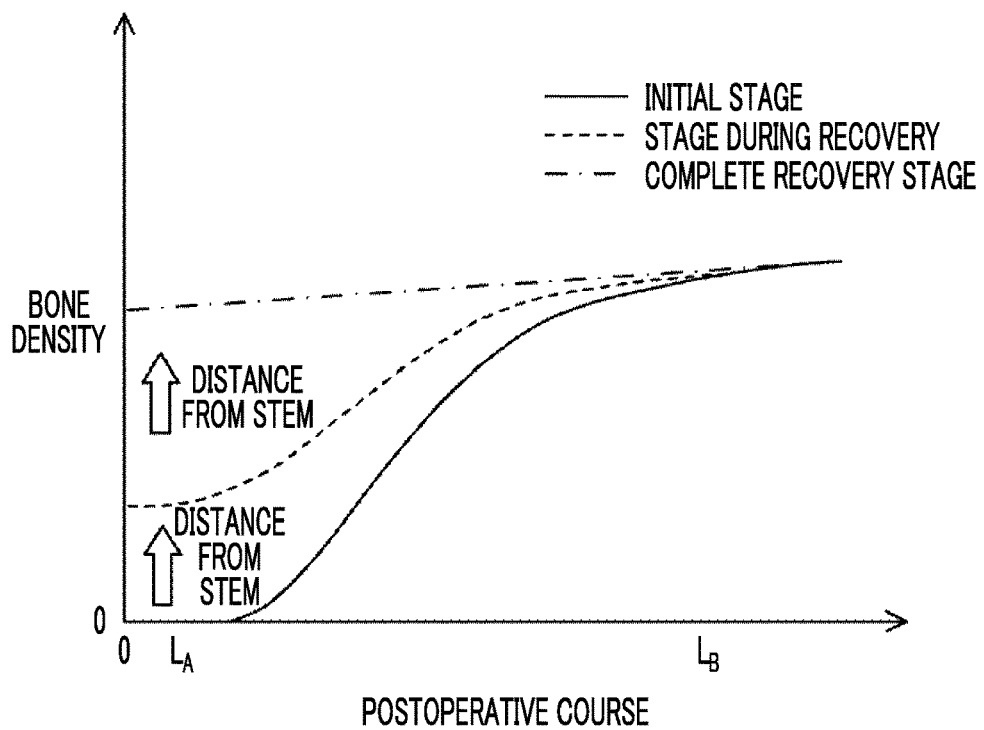
FIG. 23 is a graph showing an example of a relationship between a distance from a stem and the bone mineral density in the inside of a femur at each postoperative stage.

FIG. 23 is a graph showing an example of the relationship between the distance from the stem 81 and the bone density in the inside of the femur 80 at each postoperative stage. A horizontal axis of the graph shown FIG. 23 is a position along a straight line L in FIG. 22. In FIG. 23, a solid line corresponds to an initial stage immediately after the stem 81 is embedded in the femur 80, a dotted line corresponds to a stage during recovery, and a long dashed short dashed line corresponds to a complete recovery stage. As shown in FIG. 23, in the initial stage after the surgery, the femur 80 and the stem 81 are not intimately attached to each other, and the bone density in the vicinity of the stem 81 is extremely low. As the bone tissue grows so as to permeate the inside of the stem 81 with recovery, the bone density in the vicinity of the stem 81 is increased. On the other hand, the bone density at the distant position from the stem 81 is substantially fixed at each postoperative stage. At the complete recovery stage, the bone density in the vicinity of the stem 81 and the bone density at the distant position are substantially equivalent.

Hereinafter, an aspect in which the recovery information derivation unit 68 derives the recovery information will be described by taking a case in which the total hip joint replacement therapy shown in FIG. 22 is performed as an example. The recovery information derivation unit 68 derives a numerical value $\Delta B$ depending on a difference between a bone density $B_A$ at a position $L_A$ at which the distance from the stem 81 is relatively short and a bone density $B_B$ at a position $X_B$ at which the distance from the stem 81 is relatively long, as the recovery information. For example, the recovery information derivation unit 68 may derive the difference in the bone density ($\Delta B = B_B - B_A$) as the recovery information. In this case, the numerical value derived as the recovery information is reduced with recovery and reaches 0. In addition, the recovery information derivation unit 68 may derive the bone density ratio ($\Delta B = B_A /$ $B_B$) as the recovery information. In this case, the numerical value ΔB derived as the recovery information is increased with the recovery of the bone part and approaches 1. That is, it can be said that the numerical value ΔB depending on the difference between the bone density $B_A$ and the bone density $B_B$ is the numerical value indicating the degree of recovery of the bone part after the surgery. Therefore, by deriving the numerical value ΔB as the recovery information, it is possible to quantitatively grasp the degree of recovery of the femur 80 after the surgery.

Note that the recovery information derivation unit 68 may derive the recovery information by using the bone density per unit area in each pixel of the composite two-dimensional image C0 derived by the bone density derivation unit 63, but the recovery information may be derived by using the bone density per unit volume in each pixel of the CT image V0. In addition, also in the composite two-dimensional image C0, the pixel value of the stem 81 is significantly different from the pixel value in the bone region, so that it is possible to specify the region in which the stem 81 is present in the composite two-dimensional image C0. Therefore, the recovery information derivation unit 68 can specify the distance from the stem 81 based on the composite two-dimensional image C0.

Figure 24:
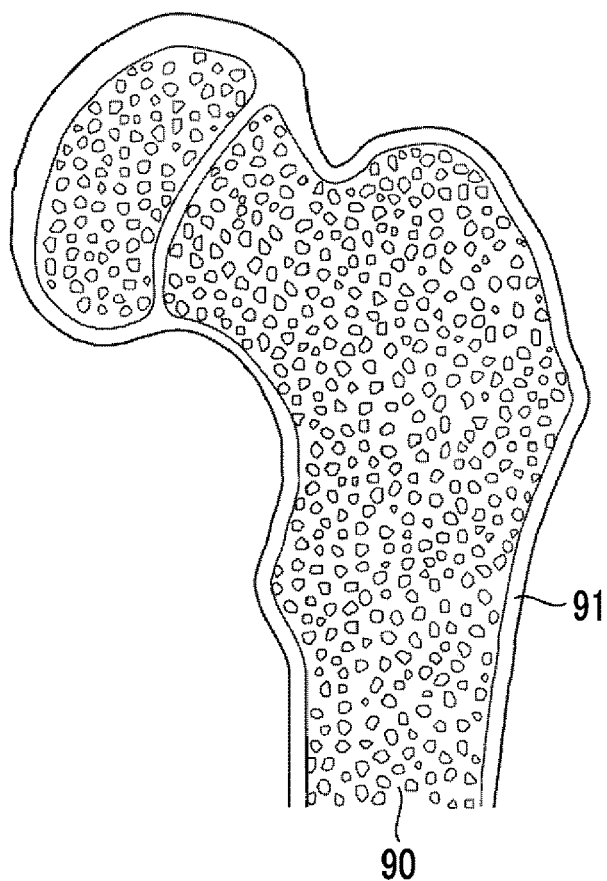
FIG. 24 is a cross-sectional view showing an example of a cross-sectional structure of a human bone.

FIG. 24 is a cross-sectional view showing an example of a cross-sectional structure of a human bone. As shown in FIG. 24, the human bone is composed of a cancellous bone 90 and a cortical bone 91 that covers the outside of the cancellous bone 90. The cortical bone 91 is harder and denser than the cancellous bone 90. The cancellous bone 90 is a collection of small bone columns called bone trabeculae that extend into the bone marrow cavity. The form of the bone trabecula includes a plate-like structure and a rod-like structure, which are connected to each other. Since the bone density of the cancellous bone 90 and the bone density of the cortical bone 91 are significantly different from each other, it is possible to distinguish the cortical bone 91 and the cancellous bone 90 from each other in the CT image V0. In particular, in a case in which the derived bone density is the bone density per unit volume, the bone density of the cancellous bone 90 and the bone density of the cortical bone 91 can be clearly distinguished from each other as compared with a case of the bone density per unit area.

In a case in which the artificial material is embedded in the cancellous bone 90, the recovery information derivation unit 68 may specify the region of the cancellous bone 90 based on the CT value of each pixel of the CT image V0, and may derive the recovery information based on the bone density of the cancellous bone 90 in the vicinity of the artificial material. Specifically, the recovery information derivation unit 68 may derive the numerical value ΔB depending on the difference between the bone density $B_A$ at a position $X_A$ in the cancellous bone 90 at which the distance from the artificial material is relatively short and the bone density $B_B$ at a position $X_B$ in the cancellous bone 90 at which the distance from the artificial material is relatively long, as the recovery information.

On the other hand, in a case in which the artificial material is embedded in the cortical bone 91, it is preferable that the recovery information derivation unit 68 specify the region of the cortical bone 91 based on the CT value of each pixel of the CT image V0, and derive the recovery information based on the bone density of the cortical bone 91 in the vicinity of the artificial material. Specifically, the recovery information derivation unit 68 may derive the numerical value ΔB depending on the difference between the bone density $B_A$ at a position $X_A$ in the cortical bone 91 at which the distance from the artificial material is relatively short and the bone density $B_B$ at a position $X_B$ in the cortical bone 91 at which the distance from the artificial material is relatively long, as the recovery information.

In a case in which the artificial material embedded in the bone part of the subject H extends to both the cancellous bone 90 and the cortical bone 91, the regions of the cancellous bone 90 and the cortical bone 91 may be specified based on the CT value of each pixel of the CT image V0, and the recovery information may be derived based on both the bone density of the cancellous bone 90 and the bone density of the cortical bone 91 in the vicinity of the artificial material. Specifically, the recovery information derivation unit 68 may derive the numerical value ΔB1 depending on the difference between the bone density $B_{A1}$ at a position $L_{A1}$ in the cancellous bone 90 at which the distance from the artificial material is relatively short and the bone density $B_{B1}$ at a position $L_{B1}$ in the cancellous bone 90 at which the distance from the artificial material is relatively long, as the recovery information, and may derive the numerical value ΔB2 depending on the difference between the bone density $B_{A2}$ at a position $L_{A2}$ in the cortical bone 91 at which the distance from the artificial material is relatively short and the bone density $B_{B2}$ at a position $L_{B2}$ in the cortical bone 91 at which the distance from the artificial material is relatively long, as the recovery information. Note that in a case in which the artificial material embedded in the bone part of the subject H extends to both the cancellous bone 90 and the cortical bone 91, the recovery information may be derived based on one of the bone density of the cancellous bone 90 and the bone density of the cortical bone 91 in the vicinity of the artificial material. That is, one of the numerical value ΔB1 or the numerical value ΔB2 may be derived as the recovery information.

Figure 25:
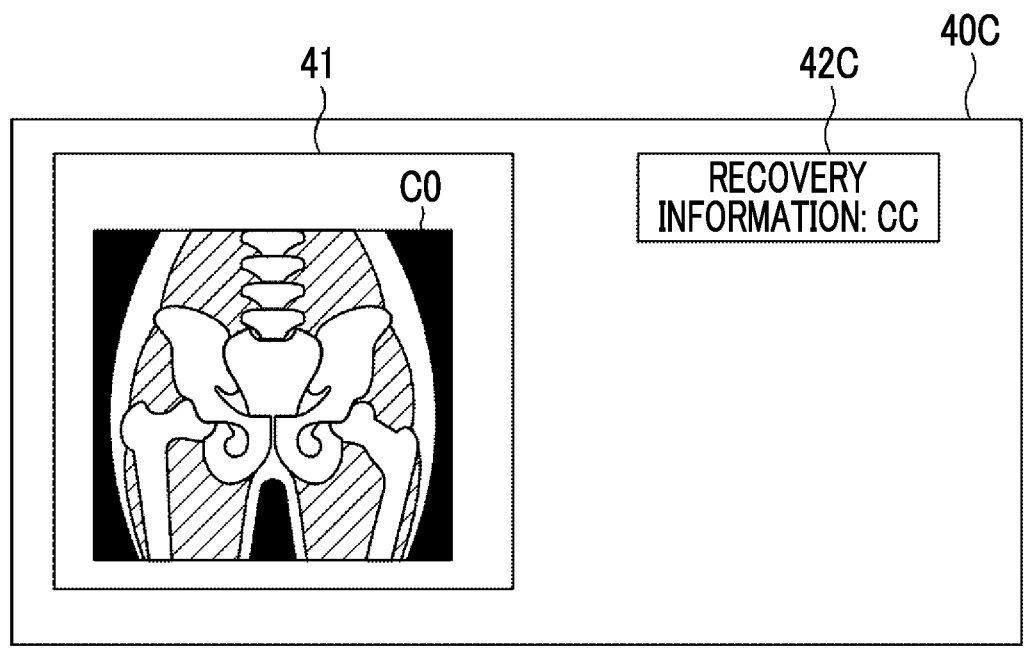
FIG. 25 is a diagram showing still another example of the teacher data.

In the third embodiment, the recovery information derived by the information derivation device 50B is used as the correct answer data of the teacher data. FIG. 25 is a diagram showing the teacher data derived in the third embodiment. As shown in FIG. 25, the teacher data 40C consists of the learning data 41 including the composite two-dimensional image C0 and correct answer data 42C which is the numerical value of the recovery information.

By learning the neural network by using the teacher data 40C shown in FIG. 25, it is possible to construct the learned neural network 23A that outputs the information representing the recovery state as the recovery information in a case in which the simple radiation image G0 is input.

In addition, in each of the embodiments described above, as the correct answer data 42 of the teacher data 40, the bone density image in which the bone density per unit area or per unit volume derived by the bone density derivation unit 63 is used as the pixel value may be used. In this case, the estimation unit 23 of the estimation device 10 derives the bone density image from the simple radiation image G0 as the result of estimation relating to the bone density. In this way, in a case in which the bone density image is derived, the bone density image may be displayed on the display screen.

Figure 26:
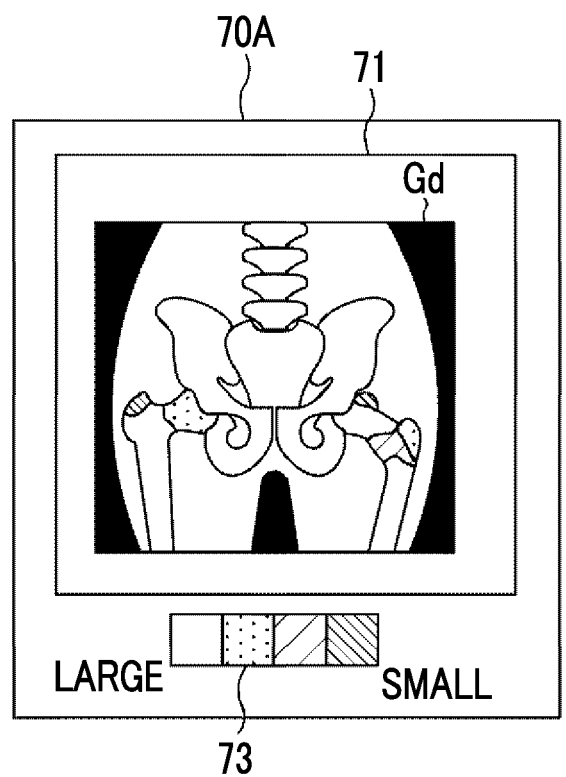
FIG. 26 is a diagram showing another example of the display screen of the result of estimation.

FIG. 26 is a diagram showing another example of the display screen of the result of estimation. As shown in FIG. 26, a display screen 70A has the image display region 71 similar to the display screen 70 shown in FIG. 14. In the image display region 71, the bone density image Gd, which is the result of estimation of the bone density in the simple radiation image G0 of the subject H, is displayed. In the bone density image Gd, a pattern is added to the bone region depending on the bone density. Note that in FIG. 26, for the sake of simplicity, the pattern representing the bone mineral density is added only to the femur. Below the image display region 71, a reference 73 representing the magnitude of the bone mineral density for the added pattern is displayed. The operator can easily recognize the bone density of the patient by interpreting the bone density image Gd with reference to the reference 73. Note that different colors may be added to the bone density image Gd depending on the bone density instead of the pattern.

In addition, in each of the embodiments described above, the information relating to the bone density of the femur in the vicinity of the hip joint is estimated, but the target bone is not limited to the femur. The technology of the present disclosure can also be applied in estimating the information relating to the bone density for any bone part, such as the femur and tibia in the vicinity of a knee joint, a vertebra, such as a lumbar vertebra, a heel bone, and a metacarpal bone.

In addition, in each of the embodiments described above, the result of estimation relating to the bone density is derived from the simple radiation image G0, but the present disclosure is not limited to this. For example, also in a case in which the result of estimation relating to the bone density is derived from the DXA scanning image obtained by imaging the subject with a DXA imaging apparatus disclosed in JP-H9-108206A (JP1997-108206A) and JP2006-271437A, the technology of the present disclosure can be applied. The DXA scanning image is the radiation image captured by the radiation detector by irradiating the subject while switching between a finely collimated high-energy radiation beam and a low-energy radiation beam and scanning. The finely collimated radiation beam is, for example, a radiation beam formed into a pencil beam, a narrow fan beam, a wide fan beam, or the like by using a collimator positioned between the radiation source and the subject. The low-energy radiation refers to radiation with a relatively lower energy than the high-energy radiation.

In this case, according to each condition, such as the pixel size of the detector that images the DXA scanning image, the scanning direction and the scanning speed at the time of imaging, the distance between the X-ray source, the subject, and the detector, or the energy distribution of the radiation (determined by the tube voltage, the target, and the filter), the image simulating the DXA scanning image may be generated from the composite two-dimensional image C0, and the learned neural network 23A may be constructed by using the generated image simulating the DXA scanning image as the learning data 41.

The image simulating the DXA scanning image need only be generated by performing, for example, processing of reducing the resolution of the composite two-dimensional image C0 depending on the pixel size of the detector used for capturing the DXA scanning image, the scanning direction, the scanning speed, or the like. Note that the image simulating the DXA scanning image is an example of a low-resolution composite two-dimensional image.

Specifically, the image simulating the DXA scanning image is generated as follows. A case will be assumed in which L, M, and N are natural numbers, and M×M pixels of the composite two-dimensional image C0 and N×N pixels of an image for learning of the DXA scanning image correspond to L mm×L mm of the actual size of the subject $H_s$. In this case, the resolution of the composite two-dimensional image C0 is reduced by setting the average value of the pixel values of (M/N)×(M/N) pixels of the composite two-dimensional image C0 to all pixel values of (M/N)×(M/N) pixels of the composite two-dimensional image C0 such that (M/N)×(M/N) pixels of the composite two-dimensional image C0, that is, a plurality of adjacent pixels correspond to one pixel of the image for learning of the DXA scanning image. Further, by performing such the resolution reduction processing in all the regions corresponding to the DXA scanning image of the composite two-dimensional image C0, the image simulating the DXA scanning image is generated. In a case in which the M/N is not a natural number, the positions of the corresponding pixels of the composite two-dimensional image C0 and the image for learning the DXA scanning image need only be appropriately adjusted by natural numbers before and behind the M/N to generate the image simulating the DXA scanning image from the composite two-dimensional image C0.

Further, as the resolution reduction processing for simulating blurriness due to scanning, the image simulating the DXA scanning image may be generated by performing the movement average processing in one direction corresponding to the scanning direction.

In addition, the image simulating the DXA scanning image may be generated by performing the movement average processing on the composite two-dimensional image C0. In the movement average processing, the size of the filter used for the calculation of the movement average and the intensity distribution of the filter need only be appropriately determined from the scanning direction and scanning speed at the time of imaging the DXA scanning image, the pixel size of the detector, the distance between the X-ray source, the subject, and the detector, and the like. For example, the resolution is lower as the scanning speed is faster, and thus the filter size need only be set relatively large. In this case, in a case in which L=10 is set, M=200 and N=5 are satisfied.

In addition, in each of the embodiments described above, the bone density, the fracture risk, and the recovery information are used as the correct answer data included in the teacher data for learning the neural network. Therefore, the information relating to the bone density estimated by the estimation unit 23 from the simple radiation image G0 is the bone density, the fracture risk, and the recovery information in the simple radiation image G0, but the present disclosure is not limited to this. The learned neural network 23A may be constructed using YAM, T score, or Z score as the correct answer data, and the YAM, the T score, and the Z score may be estimated as the information relating to the bone density from the simple radiation image G0. In addition, in the estimation unit 23, as the estimated information relating to the bone density, a result of detection of the presence or absence of the fracture, the presence or absence of the tumor, and the presence or absence of the implant may be used, or a determination result of the osteoporosis may be used. In addition, a bone disease relating to the bone density, such as multiple myeloma, rheumatism, arthritis, and cartilage hardening, may be estimated as the information relating to the bone density. In this case, the learned neural network 23A need only be constructed by using the teacher data including the information relating to the bone density as the correct answer data.

Note that in each of the embodiments described above, the estimation device 10 learns the neural network to construct the learned neural network 23A, but the present disclosure is not limited to this. The learned neural network 23A constructed in a device other than the estimation device 10 may be used for the estimation unit 23 of the estimation device 10 in the present embodiment.

In addition, in each of the embodiments described above, the estimation processing of the information relating to the bone density is performed by using the radiation image acquired by the system that images the subject H by using the radiation detector 5, it is needless to say that the technology of the present disclosure can be applied to even in a case in which the radiation image are acquired by using an accumulative phosphor sheet instead of the radiation detector.

In addition, the radiation in the embodiments described above is not particularly limited, and α-rays or γ-rays can be used in addition to X-rays.

In addition, in the embodiments described above, various processors shown below can be used as the hardware structures of processing units that execute various pieces of processing, such as the image acquisition unit 21, the information acquisition unit 22, the estimation unit 23, the learning unit 24, and the display controller 25 of the estimation device 10, and the image acquisition unit 61, the combining unit 62, and the bone density derivation unit 63 of the information derivation device 50. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. An estimation device comprising:
at least one processor,
wherein the processor functions as a learned neural network that derives a result of estimation relating to a bone density of a bone part from a simple radiation image acquired by simply imaging a subject including the bone part or a DXA scanning image acquired by imaging the subject by a DXA method, and
the learned neural network is learned by using, as teacher data, a composite two-dimensional image representing the subject, which is derived by combining a three-dimensional CT image of the subject, and information relating to the bone density of the subject.

2. The estimation device according to claim 1,
wherein the composite two-dimensional image is derived by deriving an attenuation coefficient of radiation for a composition at each position on a three-dimensional space, and projecting the CT image in a predetermined direction based on the attenuation coefficient.

3. The estimation device according to claim 1,
wherein the information relating to the bone density is obtained by specifying a bone region in the CT image, deriving an attenuation coefficient of radiation in the bone region, and deriving the information relating to the bone density based on the bone density at each position in the bone region, which is derived based on the attenuation coefficient of the radiation and a mass attenuation coefficient in the bone region.

4. The estimation device according to claim 3,
wherein the information relating to the bone density is derived by projecting the bone density at each position in the bone region in a predetermined direction.

5. The estimation device according to claim 1,
wherein the information relating to the bone density includes at least one of a bone density per unit area, a bone density per unit volume, an evaluation value of a fracture risk of the subject, or information representing a recovery state after the bone part is treated.

6. The estimation device according to claim 1,
wherein the processor functions as the learned neural network that derives the result of estimation relating to the bone density of the bone part from the DXA scanning image, and
the learned neural network is learned by using, as the teacher data, a low-resolution composite two-dimensional image obtained by performing processing for reducing a resolution on the composite two-dimensional image, and the information relating to the bone density of the subject.

7. The estimation device according to claim 6,
wherein the low-resolution composite two-dimensional image is an image in which an average value of pixel values of a plurality of adjacent pixels of the composite two-dimensional image is used as the pixel values of the plurality of adjacent pixels, and
sizes of the plurality of adjacent pixels correspond to one pixel size of the DXA scanning image.

8. The estimation device according to claim 6,
wherein the low-resolution composite two-dimensional image is an image obtained by performing movement average processing on the composite two-dimensional image in one direction, and
the one direction is a scanning direction of the DXA scanning image.

9. The estimation device according to claim 6,
wherein the low-resolution composite two-dimensional image is an image generated by generating a first low-resolution image in which an average value of pixel values of a plurality of adjacent pixels of the composite two-dimensional image is used as the pixel values of the plurality of adjacent pixels, and performing movement average processing on the first low-resolution image in one direction,
sizes of the plurality of adjacent pixels correspond to one pixel size of the DXA scanning image, and
the one direction corresponds to a scanning direction of the DXA scanning image.

10. An estimation method comprising:
using a learned neural network that derives a result of estimation relating to a bone density of a bone part from a simple radiation image acquired by simply imaging a subject including the bone part or a DXA scanning image acquired by imaging the subject by a DXA method to derive the result of estimation relating to the bone density from the simple radiation image or the DXA scanning image, wherein the learned neural network is learned by using, as teacher data, a composite two-dimensional image representing the subject, which is derived by combining a three-dimensional CT image of the subject, and information relating to the bone density of the subject.

11. A non-transitory computer-readable storage medium that stores an estimation program causing a computer to execute a procedure comprising:

using a learned neural network that derives a result of estimation relating to a bone density of a bone part from a simple radiation image acquired by simply imaging a subject including the bone part or a DXA scanning image acquired by imaging the subject by a DXA method to derive the result of estimation relating to the bone density from the simple radiation image or the DXA scanning image, wherein the learned neural network is learned by using, as teacher data, a composite two-dimensional image representing the subject, which is derived by combining a three-dimensional CT image of the subject, and information relating to the bone density of the subject.

* * * * *